United States Patent
Waki et al.

(10) Patent No.: US 9,044,175 B2
(45) Date of Patent: Jun. 2, 2015

(54) ULTRASONIC DIAGNOSTIC APPARATUS AND THREE-DIMENSIONAL ELASTIC RATIO CALCULATING METHOD

(75) Inventors: Koji Waki, Tokyo (JP); Takashi Iimura, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 533 days.

(21) Appl. No.: 13/503,987

(22) PCT Filed: Nov. 11, 2010

(86) PCT No.: PCT/JP2010/070078
§ 371 (c)(1),
(2), (4) Date: Jun. 14, 2012

(87) PCT Pub. No.: WO2011/062106
PCT Pub. Date: May 26, 2011

(65) Prior Publication Data
US 2012/0269416 A1 Oct. 25, 2012

(30) Foreign Application Priority Data
Nov. 18, 2009 (JP) .................................. 2009-262705

(51) Int. Cl.
G06K 9/00 (2006.01)
A61B 8/14 (2006.01)
A61B 8/08 (2006.01)
A61B 8/00 (2006.01)
G01S 7/52 (2006.01)
G01S 15/89 (2006.01)

(52) U.S. Cl.
CPC ... *A61B 8/14* (2013.01); *A61B 8/08* (2013.01); *A61B 8/469* (2013.01); *A61B 8/483* (2013.01); *A61B 8/485* (2013.01); *G01S 7/52036* (2013.01); *G01S 7/52042* (2013.01); *G01S 7/52063* (2013.01); *G01S 7/52087* (2013.01); *G01S 15/8993* (2013.01); *A61B 8/4254* (2013.01)

(58) Field of Classification Search
None
See application file for complete search history.

(56) References Cited

U.S. PATENT DOCUMENTS

2002/0178833 A1 12/2002 Chen et al.
2006/0285731 A1* 12/2006 Jiang et al. .................... 382/128

(Continued)

FOREIGN PATENT DOCUMENTS

CN 101065067 A 10/2007
JP A-5-317313 12/1993

(Continued)

OTHER PUBLICATIONS

International Search Report issued in International Patent Application No. PCT/JP2010/070078 dated Jan. 25, 2011.

(Continued)

*Primary Examiner* — Bhavesh Mehta
*Assistant Examiner* — Andrew Moyer
(74) *Attorney, Agent, or Firm* — Oliff PLC

(57) ABSTRACT

In order to three-dimensionally quantify the elastic information indicating the hardness or softness of tissue of an object with a simple operation, two three-dimensional regions of interest are set on a displayed elastic rendering image. A three-dimensional distortion ratio measuring unit 52 calculates a ratio between elastic information in the set first three-dimensional region of interest and elastic information in the set second three-dimensional region of interest and displays the ratio on an image display device 13.

13 Claims, 14 Drawing Sheets

(56) References Cited

U.S. PATENT DOCUMENTS

| | | |
|---|---|---|
| 2007/0100237 A1 | 5/2007 | Okamura et al. |
| 2008/0071174 A1* | 3/2008 | Waki et al. .................. 600/442 |
| 2009/0216123 A1 | 8/2009 | Matsumura et al. |

FOREIGN PATENT DOCUMENTS

| | | |
|---|---|---|
| JP | A-2007-105400 | 4/2007 |
| JP | B2-3991282 | 10/2007 |
| JP | A-2008-259555 | 10/2008 |
| JP | A-2009-45251 | 3/2009 |
| WO | WO 2006/121031 A1 | 11/2006 |
| WO | WO 2010/026823 A1 | 3/2010 |

OTHER PUBLICATIONS

Dec. 16, 2013 Office Action issued in Chinese Patent Application No. 201080052221.3.

* cited by examiner

FIG. 8
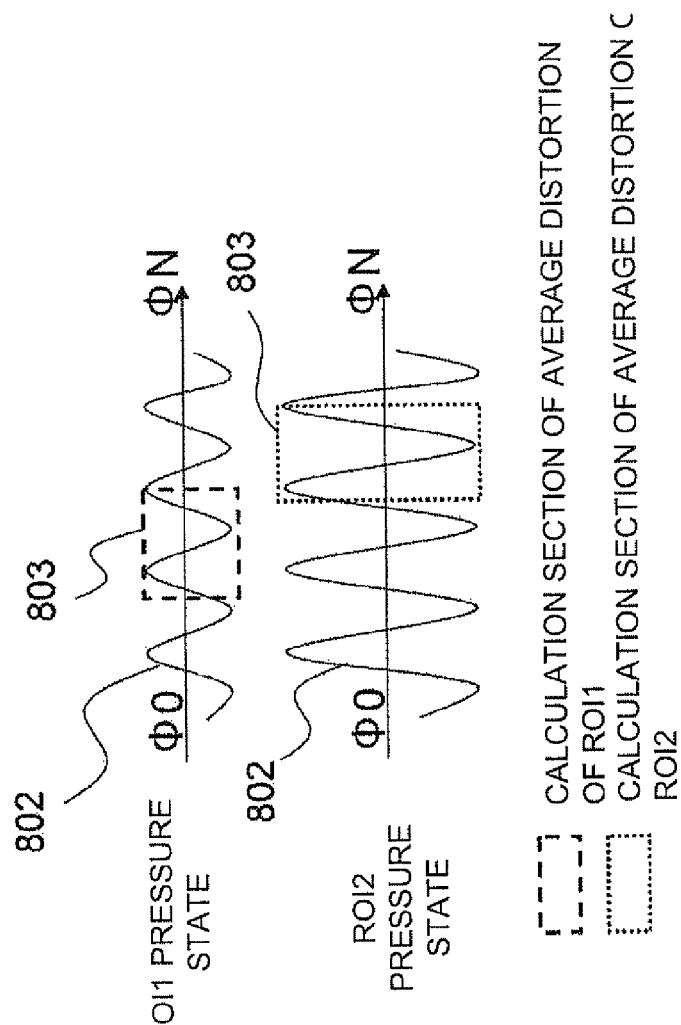
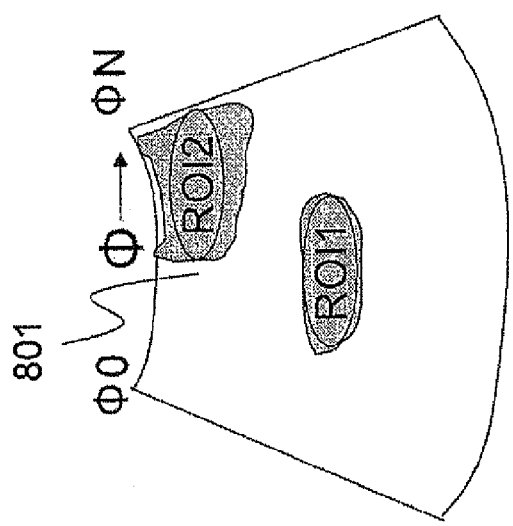

ULTRASONIC DIAGNOSTIC APPARATUS AND THREE-DIMENSIONAL ELASTIC RATIO CALCULATING METHOD

TECHNICAL FIELD

The present invention relates to an ultrasonic diagnostic apparatus and a three-dimensional elastic ratio calculating method and in particular, to a technique for three-dimensional quantification of elastic information indicating the hardness or softness of tissue of an object.

BACKGROUND ART

An ultrasonic diagnostic apparatus transmits an ultrasonic wave to the inside of an object by an ultrasonic probe including plural ultrasonic transducers, receives a reflected echo signal corresponding to the structure of body tissue from the inside of the object, generates a tomographic image, for example, a B-mode image on the basis of the reflected echo signal, and displays the B-mode image for diagnosis.

In recent years, as disclosed in PTL 1, an elastic image showing the hardness or softness of tissue of a tomographic plane has been generated by measuring an ultrasonic reception signal (RF signal) while pressing an object with an ultrasonic probe using a manual or mechanical method. That is, displacement of each part of tissue occurring due to pressure is calculated on the basis of frame data of a pair of RF signals with different tissue pressure states, frame data of elastic information such as an elastic modulus or distortion is calculated on the basis of the frame data of the calculated displacement, and an elastic image is generated and displayed on the basis of the elastic frame data.

Incidentally, the displacement of tissue changes in accordance with pressure force. Accordingly, distortion of tissue of the same part increases if the pressure is large. For this reason, an elastic image generated on the basis of distortion is only to represent a relative display of distortion of each part on the elastic image, and it is not possible to evaluate the hardness quantitatively with the elastic image.

Regarding this point, as disclosed in PTL 2, displaying an elastic image of a certain tomographic plane of an object, setting two regions of interest (ROIs) on the displayed elastic image, and calculating and displaying the two-dimensional elastic ratio of the elastic information of the two set regions of interest are known. According to this, the two-dimensional elastic ratio of the elastic information of two regions of interest is calculated as an index value. Therefore, the operator can evaluate the hardness of tissue of a diagnostic part quantitatively regardless of pressure force.

RELATED ART LITERATURE

Patent Literatures

[PTL 1] JP-A-5-317313
[PTL 2] Japanese Patent No. 3991282

OUTLINE OF INVENTION

Problems to be Solved by the Invention

However, the technique disclosed in PTL 2 is only to quantify two-dimensional elastic information on a certain tomographic plane, and quantifying the elastic information in a three-dimensional manner has not been taken into consideration.

Accordingly, in order to three-dimensionally evaluate the hardness of tissue of a diagnostic part using the technique disclosed in PTL 2, it is necessary to set two two-dimensional regions of interest on each of plural tomographic planes. However, this is not so preferable in terms of operability.

Therefore, it is an object of the invention to three-dimensionally quantify the elastic information, which indicates the hardness or softness of tissue of an object, with a simple operation.

Solution to Problem

An ultrasonic diagnostic apparatus of the invention includes: an ultrasonic probe which transmits and receives an ultrasonic wave to and from an object; an elastic information calculating unit which generates elastic frame data by calculating elastic information indicating the hardness or softness on the basis of a reflected echo signal measured by the ultrasonic probe; an elastic volume data generating unit which generates elastic volume data on the basis of the plural sets of elastic frame data; a display unit which displays at least either one of elastic slice images of plural cross sections and an elastic rendering image generated on the basis of the elastic volume data; an input unit which sets plural three-dimensional regions of interest through at least either one of the displayed elastic slice images of the plural cross sections and the displayed elastic rendering image; and a three-dimensional elastic ratio measuring unit which calculates a three-dimensional elastic ratio between the elastic information in a set first three-dimensional region of interest and the elastic information in a set second three-dimensional region of interest. The calculated three-dimensional elastic ratio is displayed on the display unit.

According to this, when an operator sets plural three-dimensional regions of interest (for example, two three-dimensional regions of interest) on an image through input means, a three-dimensional elastic ratio between the elastic information in the first three-dimensional region of interest and the elastic information in the second three-dimensional region of interest is calculated and displayed. Accordingly, the operator can grasp quantitatively the elastic information, which indicates the hardness or softness of tissue of an object, in three-dimensions with a simple operation. For example, the hardness of a three-dimensional region of interest set in a part regarded to be a lesion portion, such as a tumor, can be quantitatively expressed with a three-dimensional region of interest, which is set in a part of normal tissue or a part of tissue with little individual difference, as a reference.

Advantage of the Invention

According to the invention, an operator can quantify the elastic information, which indicates the hardness or softness of tissue of an object, in three-dimensions with a simple operation.

BRIEF DESCRIPTION OF THE DRAWINGS

FIG. 8 is a view showing the concept of processing for calculating the three-dimensional distortion ratio of the elastic information in a fifth example.

MODE FOR CARRYING OUT THE INVENTION

Figure 1:
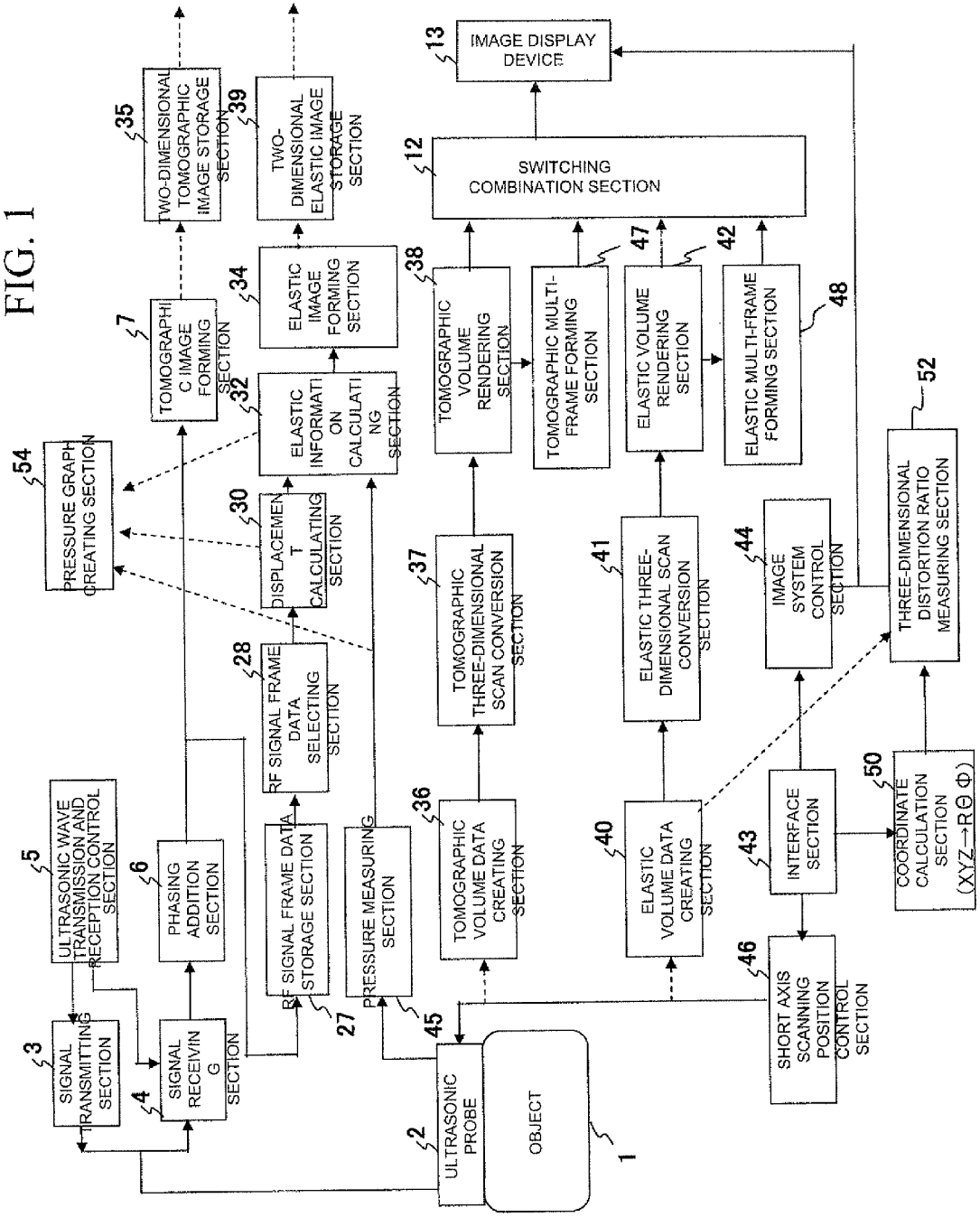
FIG. 1 is a block diagram showing the entire configuration of an ultrasonic diagnostic apparatus of the present embodiment.

Hereinafter, embodiments of an ultrasonic diagnostic apparatus and a three-dimensional quantification method of elastic information to which the invention is applied will be described. In addition, in the following explanation, the same reference numerals are given to the same functional components, and repeated explanation thereof will be omitted.

FIG. 1 is a block diagram showing the entire configuration of an ultrasonic diagnostic apparatus of the present embodiment. As shown in FIG. 1, an ultrasonic diagnostic apparatus 100 includes: an ultrasonic probe 2 used in contact with an object 1; a signal transmitting unit 3 which transmits an ultrasonic wave repeatedly to the object 1 through the ultrasonic probe 2 at intervals; a signal receiving unit 4 which receives time-series reflected echo signals generated from the object 1; an ultrasonic wave transmission and reception control unit 5 which controls switching between transmission and reception of the signal transmitting unit 3 and the signal receiving unit 4; and a phasing addition unit 6 which performs phasing addition of the reflected echo signals received by the signal receiving unit 4.

The ultrasonic probe 2 is formed by arraying plural rectangle or fan-shaped transducers, and has a function of transmitting and receiving an ultrasonic wave to and from the object 1 through the transducer. The ultrasonic probe 2 is configured to be able to be motor-controlled, so that an ultrasonic wave can be transmitted and received while shaking mechanically the transducers in a direction (short axis direction) perpendicular to the arrangement direction (long axis direction) of the plural transducers. In addition, the ultrasonic probe 2 has a position sensor which measures the inclination of a transducer simultaneously with transmission and reception of an ultrasonic wave, and outputs the inclination of a transducer as a frame number. In addition, it is also possible to use the ultrasonic probe 2 in which plural transducers are arrayed in a two-dimensional manner so that transmission and reception directions of ultrasonic waves can be electronically controlled.

The signal transmitting unit 3 drives the transducers of the ultrasonic probe 2 to generate a carrier pulse for generating an ultrasonic wave. The signal transmitting unit 3 has a function of setting the convergent point of transmitted ultrasonic waves at a certain depth. In addition, the signal receiving unit 4 generates an RF signal, that is, a received signal by amplifying the reflected echo signal received by the ultrasonic probe 2 with a predetermined gain. The ultrasonic wave transmission and reception control unit 5 controls the signal transmitting unit 3 or the signal receiving unit 4.

In addition, the ultrasonic diagnostic apparatus 100 includes: a phasing addition unit 6 which controls the phase of the input RF signal amplified by the signal receiving unit 4 and generates RF signal frame data by forming an ultrasonic beam at one or plural convergent points; a tomographic image forming unit 7 which generates tomographic image data by performing signal processing, such as gain correction, log compression, detection, contour enhancement, and filtering, on the RF signal frame data from the phasing addition unit 6; and a two-dimensional tomographic image storage unit 35 which stores the tomographic image data output from the tomographic image forming unit 7 together with the frame number.

Here, the ultrasonic diagnostic apparatus 100 of the present embodiment transmits and receives an ultrasonic wave while shaking transducers mechanically in the short axis direction through a short axis scanning position control unit 46. Accordingly, tomographic image data of n frames is stored in the two-dimensional tomographic image storage unit 35, while performing a scan in one or the opposite direction of the short axis direction.

The frame number is for matching the positions (inclinations) of plural transducers and the tomographic image data with each other. The first frame number in a scan in one direction of the short axis direction is set to "1", and the last frame number is set to "n" (n is a natural number of 2 or more). Tomographic image data of the frame number "1" is first stored in the two-dimensional tomographic image storage unit 35, and then tomographic image data of the frame number "2" is stored in the two-dimensional tomographic image storage unit 35. In addition, tomographic image data of the frame number "n" is finally stored in the two-dimensional tomographic image storage unit 35. In addition, the first frame number in a scan in the opposite direction of the short axis direction is set to "n" and the last frame number is set to "1", and the tomographic image data is sequentially stored in the two-dimensional tomographic image storage unit 35.

The ultrasonic diagnostic apparatus 100 includes a tomographic volume data generating unit 36 which reads the tomographic image data of n frames stored in the two-dimensional tomographic image storage unit 35 and generates monochrome volume data arrayed sequentially on each scan plane, so that tomographic volume data for rendering which is a group of tomographic image data in an object is generated.

In addition, the ultrasonic diagnostic apparatus 100 includes a tomographic three-dimensional scan conversion unit 37 which converts tomographic image data in the RΘΦ coordinate system, which is output from the tomographic volume data generating unit 36, to the XYZ coordinate system and a tomographic volume rendering unit 38 which generates a tomographic rendering image by projecting the tomographic image data in the XYZ coordinate system, which is output from the tomographic three-dimensional scan conversion unit 37, onto the plane.

Specifically, the tomographic volume rendering unit 38 calculates image information of each point from the brightness value and the opacity corresponding to each point (coordinates) of the tomographic volume data. In addition, the tomographic volume rendering unit 38 generates a tomographic rendering image using a volume rendering method for applying shading in which the brightness value and the opacity of the tomographic volume data in the viewing direction are calculated in the depth direction on the basis of the following Expression, for example.

$$\alpha_{outi} = \alpha_{ini} + (1 - \alpha_{ini}) * \alpha_i$$

$$c_{outi} = c_{ini} + (1 - \alpha_{ini}) * \alpha_i * c_i$$

Here, $\alpha_{outi}$: output of i-th opacity, $\alpha_{ini}$: input of i-th opacity, $\alpha i$: i-th opacity, $c_{outi}$: output of i-th brightness value, $c_{ini}$: input of i-th brightness value, and $c_i$: i-th brightness value.

Moreover, in the above, the tomographic rendering image is generated using the volume rendering method. However, it is also possible to use a surface rendering method for applying shading according to the angle of inclination of an image of each point with respect to the surface corresponding to the viewing position or a voxel method for applying shading according to the depth of an object seen from the viewing position.

In addition, the ultrasonic diagnostic apparatus 100 includes a tomographic slice image generating unit 47 which generates tomographic MPR images of orthogonal three cross sections of the tomographic volume data converted to the XYZ coordinate system by the tomographic three-dimensional scan conversion unit 37. The tomographic slice image generating unit 47 also has a function of generating plural tomographic multi-slice images cut in parallel from the tomographic volume data converted to the XYZ coordinate system in addition to the tomographic MPR image.

On the other hand, the ultrasonic diagnostic apparatus 100 includes a switching combination unit 12 which combines a tomographic rendering image and an elastic rendering image which will be described later, combines elastic MPR images or multi-slice images and elastic MPR images or an elastic multi-slice image which will be described later, displays these images in parallel, or performs switching and an image display device (display unit) 13 which displays a composite image and the like.

In addition, the ultrasonic diagnostic apparatus 100 includes: an RF signal frame data storage unit 27 which stores the RF signal frame data output from the phasing addition unit 6; an RF signal frame data selecting unit 28 which selects at least two sets of RF signal frame data stored in the RF signal frame data storage unit 27; a displacement calculating unit 30 which generates displacement frame data by measuring the displacement of body tissue of the object 1 from the two sets of RF signal frame data; an elastic information calculating unit 32 which generates elastic frame data by calculating elastic information, such as distortion, an elastic modulus, and viscosity, from the displacement information measured by the displacement measuring unit 30; and an elastic image forming unit 34 which forms two-dimensional elastic image data from the elastic information, such as the distortion or the elastic modulus, calculated by the elastic information calculating unit 32.

In addition, the ultrasonic diagnostic apparatus 100 includes: a two-dimensional elastic image storage unit 39 which stores the two-dimensional elastic image data output from the elastic image forming unit 34; an elastic volume data generating unit 40 which generates elastic volume data from the plural sets of two-dimensional elastic image data generated on plural cross sections of the object; an elastic three-dimensional scan conversion unit 41 which converts the elastic image data in the RΘΦ coordinate system, which is output from the elastic volume data generating unit 40, to the XYZ coordinate system; and an elastic volume rendering unit 42 which generates an elastic rendering image by projecting the elastic image data in the XYZ coordinate system, which is output from the elastic three-dimensional scan conversion unit 41, onto the plane.

In addition, the ultrasonic diagnostic apparatus 100 includes an elastic slice image generating unit 48 which generates an MPR image of orthogonal three cross sections of the elastic volume data converted to the XYZ coordinate system by the elastic three-dimensional scan conversion unit 41. The elastic slice image generating unit 48 also has a function of generating plural elastic multi-slice images cut in parallel from the elastic volume data converted to the XYZ coordinate system in addition to the elastic MPR image.

In addition, the ultrasonic diagnostic apparatus 100 includes an image system control unit 44, which controls each component, and an input interface unit (input unit) 43 used for various kinds of input to the image system control unit 44. The input interface unit 43 includes a keyboard, a track ball, and the like.

The RF signal frame data storage unit 27 stores sequentially the RF signal frame data generated in time series from the phasing addition unit 6. In addition, the displacement measuring unit 30 performs one-dimensional or two-dimensional correlation processing on the RF signal frame data of the selected frame number "n" to calculate a displacement or movement vector in body tissue corresponding to each point of the RF signal frame data, that is, one-dimensional or two-dimensional displacement distribution regarding the displacement direction and size. Here, in order to detect the movement vector, a block matching method is used. The block matching method is to perform processing in which an image is divided into blocks with, for example, "M×M" pixels, a block in a region of interest is observed, the most similar block to the observed block is searched for from previous frames, and a sample value is determined by predictive coding, that is, by the difference referring to this.

The elastic information calculating unit 32 calculates the distortion of body tissue corresponding to each point (coordinates) on an image from the measured value output from the displacement measuring unit 30, for example, the movement vector and the pressure value, which is output from a pressure measuring unit 45, and generates elastic information. In this case, the distortion is calculated by spatial differentiation of the amount of movement of body tissue, for example, by spatial differentiation of the displacement. In addition, the elastic information calculating unit 32 may also be configured to calculate the elastic modulus. In this case, the pressure information acquired by the pressure measuring unit 45 connected to a pressure sensor (not shown) of the ultrasonic probe 2 is output to the elastic information calculating unit 32. The elastic modulus is calculated by dividing the pressure change by a distortion change.

For example, assuming that the displacement measured by the displacement measuring unit 30 is $L(X)$ and the pressure measured by the pressure measuring unit 45 is $P(X)$ when measuring the pressure by the pressure measuring unit 45, distortion $\Delta S(X)$ can be calculated by spatial differentiation of $L(X)$. That is, the distortion $\Delta S(X)$ can be calculated using Expression $\Delta S(X) = \Delta L(X)/\Delta X$. In addition, the Young's modulus $Ym(X)$ of the elastic modulus is calculated by Expression $Ym = (\Delta P(X))/\Delta S(X)$. Since the elastic modulus of body tissue corresponding to each point of the image is calculated from the Young's modulus Ym, it is possible to acquire two-dimensional elastic images continuously. In addition, the Young's modulus is a ratio of simple tensile stress applied to the body to the tensile strain occurring in parallel to the tensile stress.

The elastic image forming unit 34 forms two-dimensional elastic image data by performing various kinds of image processing, such as smoothing processing within the coordinate plane, contrast optimization processing, and smoothing processing in the time axis direction between frames, on the calculated elastic value (distortion, an elastic modulus, and the like).

The two-dimensional elastic image storage unit 39 stores the two-dimensional elastic image data of a series of frame numbers "1" to "n". RF signal frame data of the frame numbers "1" to "n" in one direction and the opposite direction of the short axis direction of the ultrasonic probe is stored in the two-dimensional elastic image storage unit 39.

The elastic volume data generating unit 40 generates elastic volume data from the plural sets of two-dimensional elastic image data. Elastic volume data is generated by reading the two-dimensional elastic image data of n frames stored in the two-dimensional elastic image storage unit 39 and arraying the data sequentially on each scan plane. Thus, elastic volume data for rendering which is a group of two-dimensional elastic image data within the object is generated.

The elastic volume rendering unit 42 generates a three-dimensional elastic image by calculating the image information of each point from the elastic value (one of the distortion, the elastic modulus, and the like) and the opacity corresponding to each point of the elastic volume data. For example, the elastic volume rendering unit 42 generates a three-dimensional elastic image using a volume rendering method in which the elastic value of elastic volume data in the viewing direction is calculated in the depth direction. In addition, this viewing direction is the same direction as the viewing direction in volume rendering processing of the tomographic volume rendering unit 38 and the like.

$$\alpha_{outi} = \alpha_{ini} + (1 - \alpha_{ini}) \times \alpha_i$$

$$E_{outi} = E_{ini} + \alpha_i \times (1 - \alpha_{ini}) \times E_i$$

Here, $\alpha_{outi}$: output of i-th opacity, $\alpha_{ini}$: input of i-th opacity, $\alpha_i$: i-th opacity, $E_{outi}$: output of i-th elastic value, $E_{ini}$: input of i-th elastic value, and $E_i$: i-th elastic value In addition, the elastic volume rendering unit 42 gives three primary colors of light, that is, a red (R) value, a green (G) value, and a blue (B) value to the image information of the three-dimensional elastic image. For example, the elastic volume rendering unit 42 performs processing, such as giving a red code to a place with larger distortion or a smaller elastic modulus than that in the surrounding place or giving a blue code to a place with smaller distortion or a larger elastic modulus than that in the surrounding place.

For example, only the tomographic rendering image data or the elastic rendering image data can also be extracted by setting α to 0 or 1. The image selecting unit selects an image, which is to be displayed on the image display device 13, from the tomographic rendering image data and the elastic rendering image data in the volume memory and the composite image data of the image processing unit.

The switching combination unit 12 combines a tomographic rendering image and an elastic rendering image, which are stored in the image memory, by changing the combination ratio, for example. The switching combination unit 12 reads the tomographic rendering image and the elastic rendering image at the same viewing position from the image memory. Moreover, although the tomographic rendering image and the elastic rendering image are combined, the tomographic rendering image and the elastic rendering image are added in a substantially two-dimensional manner since the tomographic rendering image and the elastic rendering image are image data after volume rendering processing and the like.

Specifically, for example, as shown in the following Expression, each of the red (R), green (G), and blue (B) values of the elastic rendering image and each of the red (R), green (G), and blue (B) values of the tomographic rendering image are added at each point. In addition, α is a coefficient equal to or larger than 0 and equal to or smaller than 1, and can be arbitrarily set by the input interface unit 43.

(composite image data R)=α×(elastic rendering image data R)+(1−α)×(tomographic rendering image data R)

(composite image data G)=α×(elastic rendering image data G)+(1−α)×(tomographic rendering image data G)

(composite image data B)=α×(elastic rendering image data B)+(1−α)×(tomographic rendering image data B)

Incidentally, in the ultrasonic diagnostic apparatus 100 which generates an elastic image by calculating the displacement of tissue of an object as in the present embodiment, the displacement of tissue changes in accordance with the pressure force by the ultrasonic probe, for example. Accordingly, distortion of tissue of the same part increases if the pressure is large.

Then, by setting two regions of interest (ROI) which are set on an elastic image of a certain tomographic plane of the object and calculating the ratio of the elastic information on the two set regions of interest, the elastic information of a diagnostic part is set as an index value to evaluate the hardness quantitatively.

This method will be briefly described. As described above, the displacement of tissue changes in accordance with the pressure force of the ultrasonic probe, for example. Therefore, an elastic image generated on the basis of the amount of distortion is only to represent a relative display of distortion of each part on the elastic image, and it is not possible to evaluate the hardness quantitatively with the elastic image. In contrast, for example, the elastic modulus (E) is obtained by dividing stress (σ) applied to tissue by distortion (ε). Accordingly, since the elastic modulus (E) is an absolute value indicating the hardness or softness of tissue, quantitative evaluation is possible.

In the method described above, for example, a region of interest is set in a place considered to be cancer tissue and a place considered to be fat tissue, and the distortion ratio in the two regions of interest is calculated. That is, assuming that the elastic moduli of tissue in which the two regions of interest are set is set to $E_1$ and $E_2$, Expressions of $E_1 = \sigma_1/\epsilon_1$ and $E_2 = \sigma_2/\epsilon_2$ are satisfied. Here, it can be estimated that almost the same pressure is applied to tissue of the same frame. That is, $\sigma_1 \cong \sigma^2$ can be estimated. In the method described above, using this point, the ratio $E_1/E_2$ of the elastic moduli in the two regions of interest is estimated by calculating the distortion ratio $\epsilon_1/\epsilon_2$.

The ultrasonic diagnostic apparatus 100 of the present embodiment includes a coordinate transformation unit 50, a three-dimensional distortion ratio measuring unit 52, and the like as characteristic components, as shown in FIG. 1. The three-dimensional distortion ratio measuring unit 52 is a three-dimensional elastic ratio measuring unit which, when first and second three-dimensional regions of interest are set on an elastic rendering image or the like displayed on the image display device 13 through the input interface unit 43, calculates a three-dimensional elastic ratio between the elastic information in the set first three-dimensional region of interest and the elastic information in the set second three-dimensional region of interest. That is, the three-dimensional distortion ratio measuring unit 52 can be replaced with the three-dimensional elastic ratio measuring unit.

The three-dimensional distortion ratio measuring unit (three-dimensional elastic ratio measuring unit) calculates a two-dimensional elastic ratio between the elastic information of a region corresponding to the first three-dimensional region of interest and the elastic information of a region corresponding to the second three-dimensional region of interest in each of plural sets of elastic frame data of the elastic rendering image. In addition, the three-dimensional distortion ratio measuring unit 52 (three-dimensional elastic ratio measuring unit) calculates a three-dimensional elastic ratio on the basis of the two-dimensional elastic ratio in each set of elastic frame data. Specifically, the three-dimensional distortion ratio measuring unit 52 (three-dimensional elastic ratio measuring unit) calculates the three-dimensional elastic ratio by averaging the two-dimensional elastic ratios calculated in each set of elastic frame data.

In addition, the coordinate transformation unit 50 is coordinate transformation means for transforming each three-dimensional region of interest from the XYZ coordinate system to the RΘΦ coordinate system when first and second three-dimensional regions of interest are set through the input interface unit 43 on an elastic rendering image in the XYZ coordinate system displayed on the image display device 13, for example. Hereinafter, the feature configuration of the present embodiment will be described in detail by way of examples.

First Example

Figure 2:
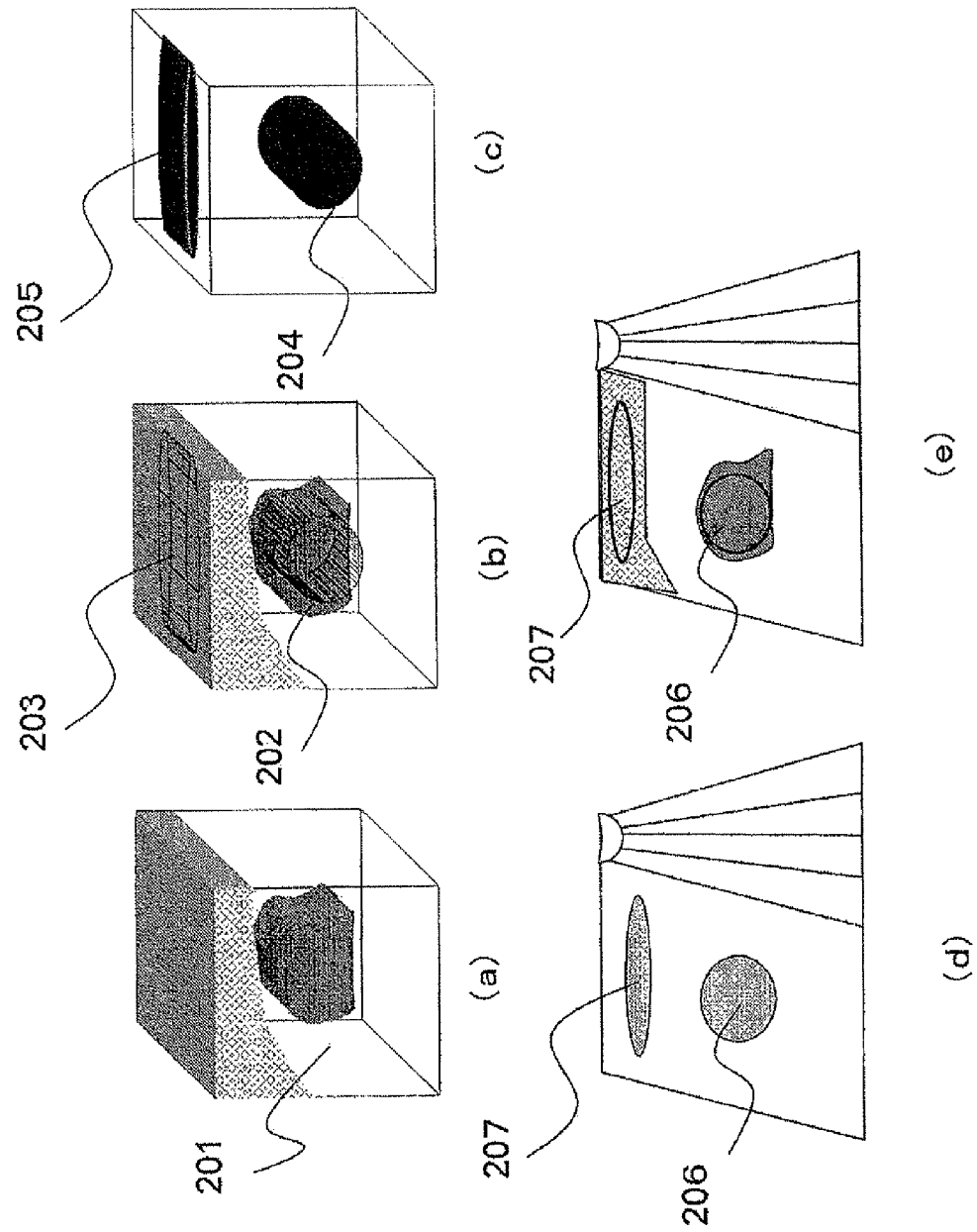
FIG. 2 is a view showing the concept of processing for calculating the three-dimensional distortion ratio of the elastic information in a first example.
Figure 3:
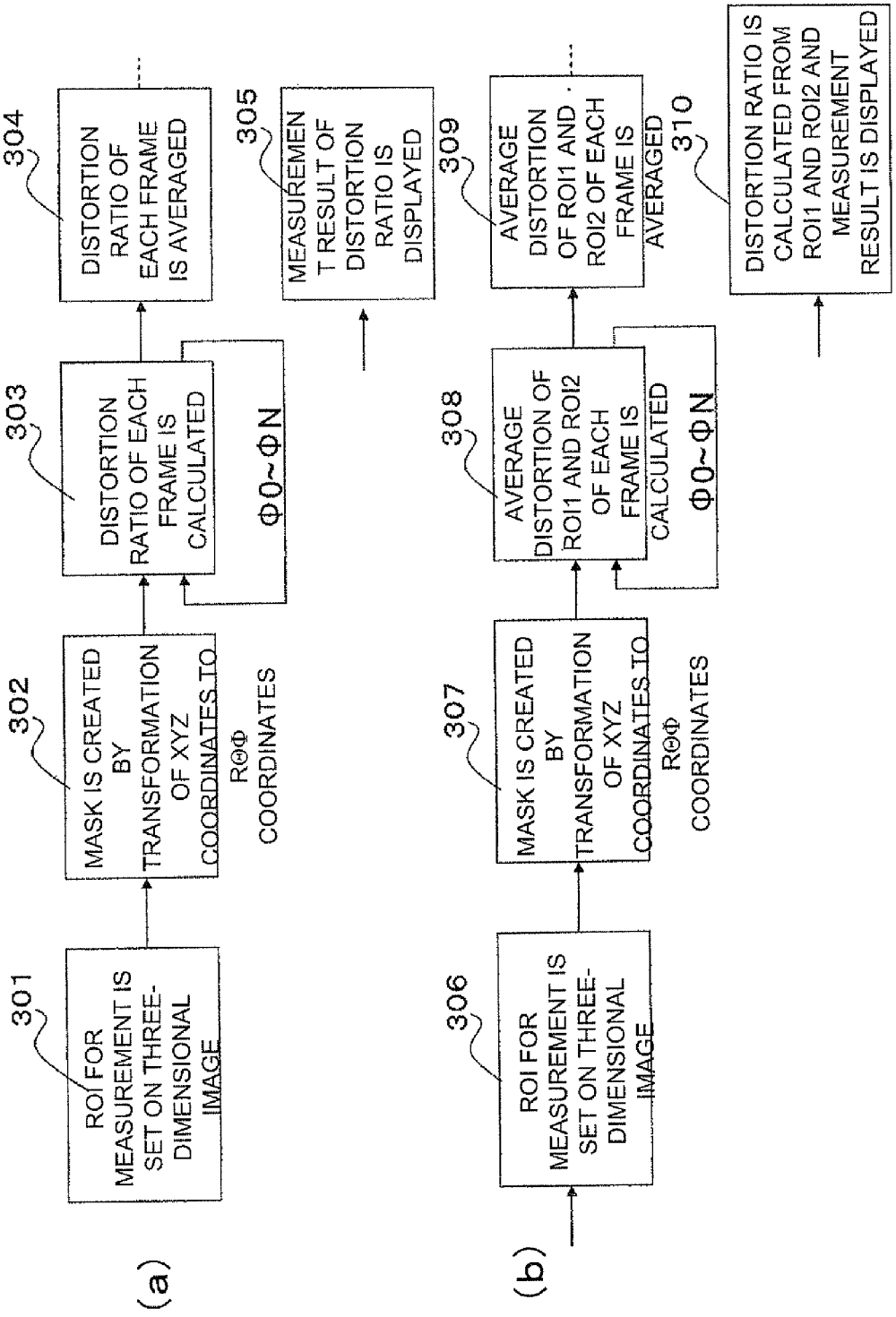
FIG. 3 is a flow chart of the processing in the first example.

A first example of calculating the three-dimensional elastic ratio (three-dimensional distortion ratio) of the elastic information on the ultrasonic diagnostic apparatus of the present embodiment will be described using FIGS. 2 and 3. FIG. 2 is a view showing the concept of processing for calculating the three-dimensional distortion ratio of the elastic information in the first example. FIG. 3 is a flow chart of the processing in the first example. This example is an example when an elastic rendering image generated on the basis of the elastic volume data converted to the XYZ coordinate system by the elastic three-dimensional scan conversion unit 41 is displayed and two regions of interest are set on the elastic rendering image.

First, as shown in FIG. 2(a), an elastic rendering image 201 is displayed on the image display device 13. As shown in FIGS. 2(b) and 3(a), an operator sets two three-dimensional regions of interest 202 and 203 on the elastic rendering image 201 through the input interface unit 43 so as to be transparent or overwritten (301 in FIG. 3). Hereinafter, the two three-dimensional regions of interest 202 and 203 are appropriately called ROI1 and ROI2.

Then, as shown in FIG. 2(c), the three-dimensional regions of interest 202 and 203 are made as data, that is, as mask information items 204 and 205 of XYZ data. Then, as shown in FIG. 2(d), the mask information items 204 and 205 are coordinate-transformed from the Cartesian coordinate system of XYZ to the polar coordinate system of RΘΦ by the coordinate transformation unit 50. As a result, ROI mask data sets 206 and 207 in the RΘΦ coordinate system are created (302 in FIG. 3).

The three-dimensional distortion ratio measuring unit 52 can refer to the elastic information (distortion) of the three-dimensional region of interest, which is set in the XYZ coordinate system from the elastic information volume data in the RΘΦ coordinate system, by ON/OFF control of the ROI mask data sets 206 and 207, as shown in FIG. 2(e). As a result, a three-dimensional elastic ratio is calculated on the basis of the elastic information of the ROI mask data 206 and the elastic information of the ROI mask data 207 converted to the RΘΦ coordinate system.

More specifically, the three-dimensional distortion ratio measuring unit 52 calculates distortion (average value) in each of the ROI1 and the ROI2 of the elastic frame data as shown in Expressions 1 and 2. Then, the ratio of distortion between the ROI1 and the ROI2 is calculated as shown in Expression 3 (303 in FIG. 3). As a result, it is possible to calculate the distortion ratio for each item of elastic frame data. Finally, as shown in Expression 4, a three-dimensional distortion ratio is calculated by averaging the two-dimensional distortion ratio calculated for each item of the elastic frame data (304 in FIG. 3). The calculated three-dimensional distortion ratio is displayed on the image display device 13 (305 in FIG. 3).

$$\varepsilon_{roi1}(\phi) = \frac{\sum_{i=rstart}^{rend} \sum_{j=tstart}^{tend} \varepsilon_{ij}(\phi)}{i \times j} : (ROI1) \quad \text{[Expression 1]}$$

$$\varepsilon_{roi2}(\phi) = \frac{\sum_{i=rstart}^{rend} \sum_{j=tstart}^{tend} \varepsilon_{ij}(\phi)}{i \times j} : (ROI2) \quad \text{[Expression 2]}$$

$$SR(\phi) = \frac{\varepsilon_{roi1}(\phi)}{\varepsilon_{roi2}(\phi)} \quad \text{[Expression 3]}$$

$$SR^{3d} = \frac{\sum_{\phi=start\phi}^{end\phi} SR(\phi)}{N_\phi} \quad \text{[Expression 4]}$$

Here, $\varepsilon_{ij}(\phi)$: pixel distortion at RΘΦ coordinates (i,j,φ), $\varepsilon_{roi1}(\phi)$: average distortion within ROI1 in a frame, $\varepsilon_{roi2}(\phi)$: average distortion within ROI2 in a frame, SR(φ): distortion ratio between frames, $SR^{3d}(\phi)$: average distortion in three dimensions, and $N_\phi$: the number of frames of averaged elastic frame data.

On the other hand, although the above is an explanation in the case of FIG. 3(a), it is also possible to perform a procedure shown in FIG. 3(b). First, the ROI1 and the ROI2 are set on a three-dimensional image (306 in FIG. 3), and a measured ROI mask is converted from the XYZ coordinates to the RΘΦ coordinates (307 in FIG. 3).

Then, the average distortion value of elastic frame data is calculated from the elastic information volume data in the RΘΦ coordinate system (308 in FIG. 3), and the average distortion values of the elastic frame data are averaged from the ROI1 and the ROI2 of the elastic frame data (309 in FIG. 3). Finally, the distortion ratio is calculated from the ratio of the average distortion values of the ROI1 and the ROI2 and is displayed (310 in FIG. 3). In the case of this procedure, the three-dimensional average distortion values in the ROI1 and the ROI2 are calculated from Expressions 5 and 6, and the average value of the distortion ratios of the ROI1 and the ROI2 in three dimensions is calculated from Expression 7.

$$\varepsilon_{roi1}^{3d} = \frac{\sum_{k=\phi start}^{\phi end} \sum_{i=rstart}^{rend} \sum_{j=tstart}^{tend} \varepsilon_{ijk}}{i \times j \times k} : (ROI1)$$ [Expression 5]

$$\varepsilon_{roi2}^{3d} = \frac{\sum_{k=\phi start}^{\phi end} \sum_{i=rstart}^{rend} \sum_{j=tstart}^{tend} \varepsilon_{ijk}}{i \times j \times k} : (ROI2)$$ [Expression 6]

$$SR^{3d} = \frac{\varepsilon_{roi1}^{3d}}{\varepsilon_{roi2}^{3d}}$$ [Expression 7]

Here, $\varepsilon_{roi1}{}^{3d}$: average three-dimensional distortion within ROI1, $\varepsilon_{roi2}{}^{3d}$: average three-dimensional within ROI2, and $\varepsilon_{ijk}$: pixel distortion in RΘΦ coordinates (j, j, k).

Incidentally, when three-dimensional regions of interest are set on an elastic rendering or the like displayed in the XYZ coordinate system, elastic information, for example, on the XY cross section, the YZ cross section, and the XZ cross section in the XYZ coordinate system is not necessarily generated in the same pressure state. Therefore, if the ratio of elastic information on the XY cross section, the YZ cross section, and the XZ cross section is calculated, for example, it is not possible to realize appropriate quantification. Regarding this point, the three-dimensional elastic information can be appropriately quantified by transforming the first and second three-dimensional regions of interest, which are set on an elastic rendering image or the like in the XYZ coordinate system, from the XYZ coordinate system to the RΘΦ coordinate system and calculating a three-dimensional elastic ratio on the basis of the elastic information of the first and second three-dimensional regions of interest converted to the RΘΦ coordinate system as in the present embodiment.

Moreover, in this example, an example of the case where the ROI1 and the ROI2 for measurement are set using an elastic rendering image as positional information has been described. However, the ROI1 and the ROI2 for measurement may also be set on a tomographic rendering image or on a composite rendering image in which a tomographic image and an elastic image overlap each other.

Here, coordinate transformation from the Cartesian coordinate system of XYZ to the polar coordinate system of RΘΦ by the coordinate transformation unit 50 will be described. $x_i$, $y_i$, and $z_i$ are calculated from the coordinates X and Y on a screen and a matrix for MPR using Expression 8, and each pixel is converted from the screen 2D coordinates to the XYZ coordinates.

$$\begin{pmatrix} x_i \\ y_i \\ z_i \\ 1 \end{pmatrix} = \begin{pmatrix} M_{00} & M_{01} & M_{02} & M_{03} \\ M_{10} & M_{11} & M_{12} & M_{13} \\ M_{20} & M_{21} & M_{22} & M_{23} \\ M_{30} & M_{31} & M_{32} & M_{33} \end{pmatrix} \begin{pmatrix} X \\ Y \\ 0 \\ 1 \end{pmatrix}$$ [Expression 8]

In addition, from Expression 9, coordinate transformation is performed on the short axis plane in the XYZ coordinate system using the affine matrix. Then, conversion to the polar coordinates is performed from Expressions 10 and 11, and intermediate coordinates of φ and γ are calculated from offset and scale of the coordinates in Expressions 12 to 15.

$$\begin{pmatrix} u_1 \\ v_1 \\ 1 \end{pmatrix} = \begin{pmatrix} A_1 & B_1 & C_1 \\ A_1 & B_1 & C_1 \\ 1 & 1 & 1 \end{pmatrix} \begin{pmatrix} y_i \\ z_i \\ 1 \end{pmatrix}$$ [Expression 9]

$$vv_1 = \mathrm{atan}(v_1/u_1)$$ [Expression 10]

$$uu_1 = \sqrt{v_1^2 + u_1^2}$$ [Expression 11]

$$\phi' = vv_1 + \phi_{offset}$$ [Expression 12]

$$\phi_i = \phi' * \phi_{scale}$$ [Expression 13]

$$r'_{tmp} = uu_1 + r_{offset3d}$$ [Expression 14]

$$r_{tmp} = r'_{tmp} * r_{scale3d}$$ [Expression 15]

Then, from Expression 16, conversion to the Cartesian coordinates in the long axis direction is performed on the basis of $x_i$ of the XYZ coordinates, the above-calculated $r_{tmp}$, and the of fine matrix coefficient. Then, conversion to the polar coordinates is performed from Expressions 17 and 18.

$$\begin{pmatrix} u_2 \\ v_2 \\ 1 \end{pmatrix} = \begin{pmatrix} A_1 & B_1 & C_1 \\ A_1 & B_1 & C_1 \\ 1 & 1 & 1 \end{pmatrix} \begin{pmatrix} x_i \\ r_{tmpi} \\ 1 \end{pmatrix}$$ [Expression 16]

$$vv_2 = \mathrm{atan}(v_2/u_2)$$ [Expression 17]

$$uu_2 = \sqrt{v_2^2 + u_2^2}$$ [Expression 18]

In addition, from Expressions 19 to 22, intermediate coordinates of γ and θ are calculated from the offset and the scale of the coordinates. Accordingly, it becomes possible to refer to a polar coordinate voxel corresponding to the MPR plane.

$$\theta' = vv_1 \theta_{offset}$$ [Expression 19]

$$\theta_i = \theta' * \theta_{scale}$$ [Expression 20]

$$r_i' = uu_2 r_{offset2d}$$ [Expression 21]

$$r_i = r_i' * r_{scale2d}$$ [Expression 22]

As described above, in this example, there are provided the ultrasonic probe 2 which transmits and receives an ultrasonic wave to and from an object, the elastic information calculating unit 32 which generates elastic frame data by calculating the elastic information indicating the hardness or softness on the basis of a reflected echo signal measured by the ultrasonic probe 2, the elastic volume data generating unit 40 which generates elastic volume data on the basis of plural sets of elastic frame data, the display unit 13 which displays at least either one of elastic slice images of plural cross sections and an elastic rendering image generated on the basis of the elastic volume data, the input unit 43 which sets plural three-dimensional regions of interest through at least either one of the displayed elastic slice images of the plural cross sections and the displayed elastic rendering image, and the three-dimensional distortion ratio measuring unit 52 (three-dimensional elastic ratio measuring unit) which calculates a three-dimensional elastic ratio between the elastic information in the set first three-dimensional region of interest and the elastic information in the set second three-dimensional region of interest. The calculated three-dimensional elastic ratio is displayed on the display unit 13. Accordingly, the operator can grasp quantitatively the elastic information, which indicates the hardness or softness of tissue of an object, in three-dimensions with a simple operation.

In particular, in order to generate the elastic frame data of plural tomographic planes with different slice positions of the object, it is necessary to transmit and receive an ultrasonic wave while sliding on the ultrasonic scan plane in the short axis direction using an ultrasonic probe capable of motor-controlling the ultrasonic scan plane in the short axis direction of the probe, for example. On the other hand, as described above, an elastic image is generated while pressing an object with an ultrasonic probe using a manual or mechanical method. Accordingly, the elastic frame data generated on the plural tomographic planes of the object is generated in different pressure states. Here, since the same pressure force is applied to the same elastic frame data, the influence of pressure force can be eliminated by calculating the ratio of elastic information of two two-dimensional regions of interest. As a result, quantification of elastic information can be realized. However, appropriate quantification cannot be achieved even if the ratio of elastic information between two sets of elastic frame data generated in different pressure state of different tomographic planes is calculated.

Regarding this point, the three-dimensional distortion ratio measuring unit 52 (three-dimensional elastic ratio measuring unit) calculates a two-dimensional elastic ratio between the elastic information of a region corresponding to the first three-dimensional region of interest and the elastic information of a region corresponding to the second three-dimensional region of interest in each of the plural sets of elastic frame data of the elastic rendering image, and calculates a three-dimensional elastic ratio on the basis of the two-dimensional elastic ratio in each set of the elastic frame data. The three-dimensional distortion ratio measuring unit 52 (three-dimensional elastic ratio measuring unit) calculates the three-dimensional elastic ratio by averaging the two-dimensional elastic ratios calculated in each set of the elastic frame data.

According to this, the ratio of elastic information in each of the plural tomographic planes where elastic frame data is generated is calculated. Therefore, even if plural sets of elastic frame data are generated in different pressure states, quantification of the three-dimensional elastic information can be appropriately realized.

More specifically, when the elastic volume data is generated in the RΘΦ coordinate system, the ultrasonic diagnostic apparatus of the invention is configured to include: the elastic three-dimensional scan conversion unit 41 which converts elastic volume data from the RΘΦ coordinate system to the XYZ coordinate system; the elastic volume rendering unit 42 which generates an elastic rendering image on the basis of the elastic volume data converted to the XYZ coordinate system; and the coordinate transformation unit 50 which converts the first and second three-dimensional regions of interest, which are set on the elastic rendering image in the XYZ coordinate system displayed on the image display device 13 (display unit), from the XYZ coordinate system to the RΘΦ coordinate system. The three-dimensional distortion ratio measuring unit 52 (three-dimensional elastic ratio measuring unit) may be configured to calculate the three-dimensional elastic ratio on the basis of the elastic information of the first three-dimensional region of interest and the elastic information of the second three-dimensional region of interest which have been converted to the RΘΦ coordinate system.

Moreover, in order to display various images, such as an elastic rendering image, on the image display device 13 (display unit) on the basis of the elastic volume data generated in the RΘΦ coordinate system, it is general to convert the elastic volume data in the RΘΦ coordinate system to that in the XYZ coordinate system and generate and display an elastic rendering image or the like on the basis of the elastic volume data in the XYZ coordinate system. Here, when three-dimensional regions of interest are set on an elastic rendering or the like displayed in the XYZ coordinate system, elastic information, for example, on the XY cross section, the YZ cross section, and the XZ cross section in the XYZ coordinate system is not necessarily generated in the same pressure state. Therefore, if the ratio of elastic information on the XY cross section, the YZ cross section, and the XZ cross section is calculated, for example, it is not possible to realize appropriate quantification. Regarding this point, in the invention, the first and second three-dimensional regions of interest, which are set on an elastic rendering image or the like in the XYZ coordinate system, are converted from the XYZ coordinate system to the RΘΦ coordinate system and a three-dimensional elastic ratio is calculated on the basis of the elastic information of the first and second three-dimensional regions of interest converted to the RΘΦ coordinate system. Therefore, the three-dimensional elastic information can be appropriately quantified.

More specifically, the three-dimensional distortion ratio measuring unit 52 (three-dimensional elastic ratio measuring unit) may be configured to calculate a ratio between the elastic information of a region corresponding to the first three-dimensional region of interest and the elastic information of a region corresponding to the second three-dimensional region of interest, which are converted to the RΘΦ coordinate system, in each of the plural tomographic planes, in which the pressure state of tissue of the object in the RΘΦ coordinate system is the same, and calculate a three-dimensional elastic ratio on the basis of the calculated two-dimensional elastic ratio in the plural tomographic planes.

Second Example

A second example of the ultrasonic diagnostic apparatus of the present embodiment will be described. This example is different from the first example in that the elastic slice image generating unit 48 generates an MPR image of orthogonal three cross sections of the elastic volume data converted to the XYZ coordinate system and sets first and second three-dimensional regions of interest on the displayed MPR image in the XYZ coordinate system. Accordingly, explanation regarding a portion overlapping the first embodiment will be omitted.

Figure 4:
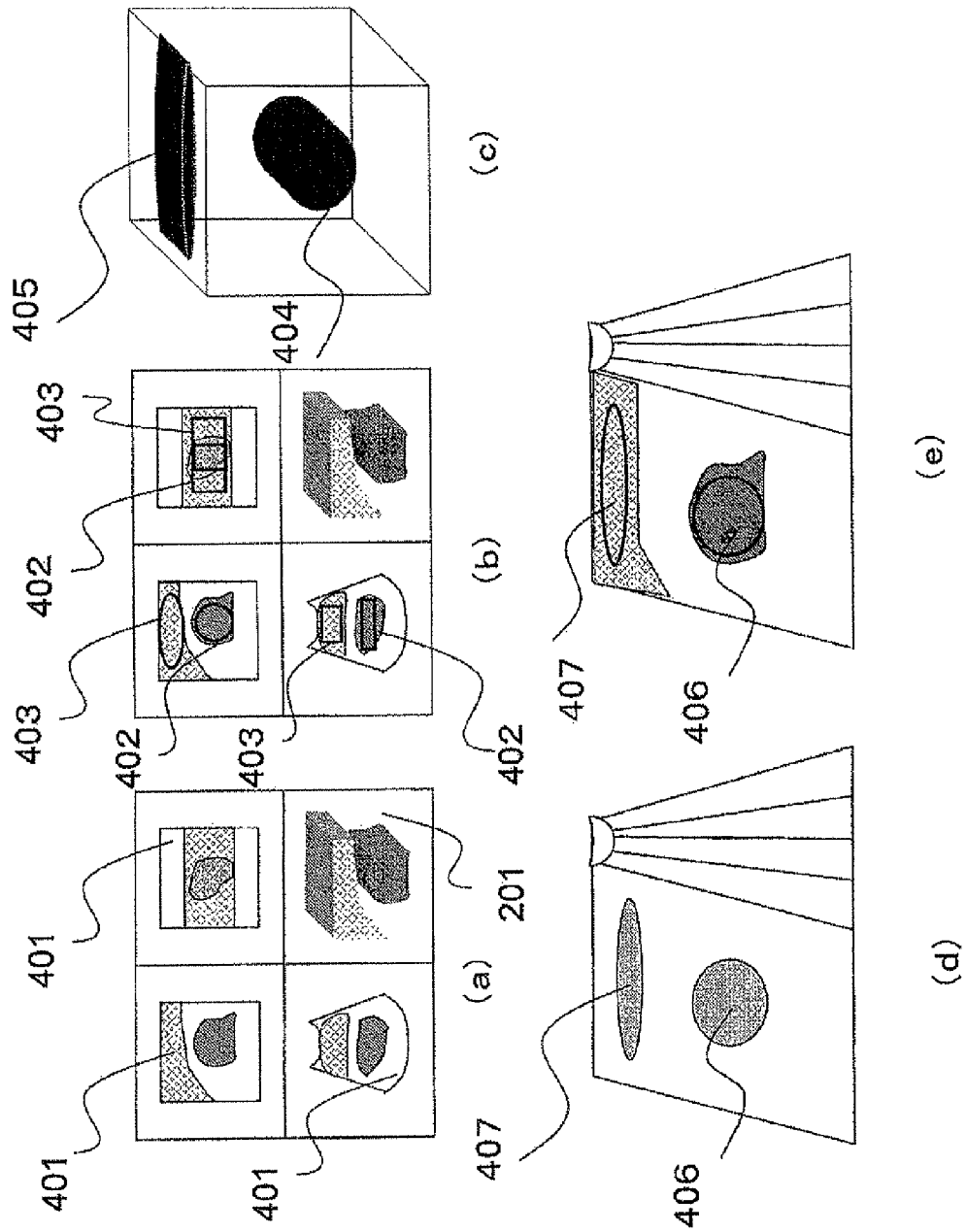
FIG. 4 is a view showing the concept of processing for calculating the three-dimensional distortion ratio of the elastic information in a second example.

FIG. 4 is a view showing the concept of processing for calculating the three-dimensional elastic ratio (three-dimensional distortion ratio) of the elastic information in the second example. First, as shown in FIG. 4(a), an MPR image 401 and an elastic rendering image 201 are displayed on the image display device 13. Specifically, elastic images of the XY plane, the YZ plane, and the XZ plane in the XYZ coordinate system are displayed as the MPR image 401 in upper left, lower left, and upper right regions of four divided regions of the screen, and the elastic rendering image 201 is displayed in a lower right region of the screen. However, the elastic rendering image 201 may not be displayed.

As shown in FIG. 4(b), an operator sets two three-dimensional regions of interest 402 and 403 on the MPR image 401 through the input interface unit 43. Hereinafter, the two three-dimensional regions of interest 402 and 403 are appropriately called ROI1 and ROI2. By setting the ROI1 and the ROI2 on the MPR image as described above, it is possible to check the setting state of the ROI in each cross section. For example, in the case of a tumor which is long and narrow in the Z direction, it is possible to adjust the ROI easily.

Then, as shown in FIG. 4(c), the three-dimensional regions of interest 402 and 403 are made as data, that is, as mask information items 404 and 405 of XYZ data. That is, as shown in FIG. 4(b), the ROI information set on the MPR image is two-dimensional information visually, but is information to be managed as XYZ coordinates. Accordingly, the ROI information set on the MPR image can be easily made as data, that is, as mask information of XYZ data shown in FIG. 4(c). Then, as shown in FIG. 4(d), the mask information items 404 and 405 are coordinate-transformed from the Cartesian coordinate system of XYZ to the polar coordinate system of RΘΦ by the coordinate transformation unit 50. As a result, ROI mask data 406 and 407 in the RΘΦ coordinate system are generated.

The three-dimensional distortion ratio measuring unit 52 can refer to the elastic information (distortion) of the three-dimensional region of interest, which is set in the XYZ coordinate system from the elastic information volume data in the RΘΦ coordinate system, by ON/OFF control of the ROI mask data 406 and 407, as shown in FIG. 4(e). As a result, a three-dimensional elastic ratio is calculated on the basis of the elastic information of the ROI mask data 406 and the elastic information of the ROI mask data 407 converted to the RΘΦ coordinate system. The method of calculating the three-dimensional elastic ratio is the same as that in the first example.

In this example, setting the ROI1 and the ROI2 for measurement using elastic MPR images as positional information has been described. However, the invention is not limited to this, and the ROI1 and the ROI2 for measurement may also be set on tomographic NPR images or on a composite MPR image in which a tomographic image and an elastic image overlap each other.

Third Example

A third example of the ultrasonic diagnostic apparatus of the present embodiment will be described. This example is different from the first example in that the elastic slice image generating unit 48 generates plural multi-slice images (elastic multi-slice images) cut in parallel from the elastic volume data converted to the XYZ coordinate system and sets first and second three-dimensional regions of interest on the displayed multi-slice image in the XYZ coordinate system. Accordingly, explanation regarding a portion overlapping the first embodiment will be omitted.

Figure 5:
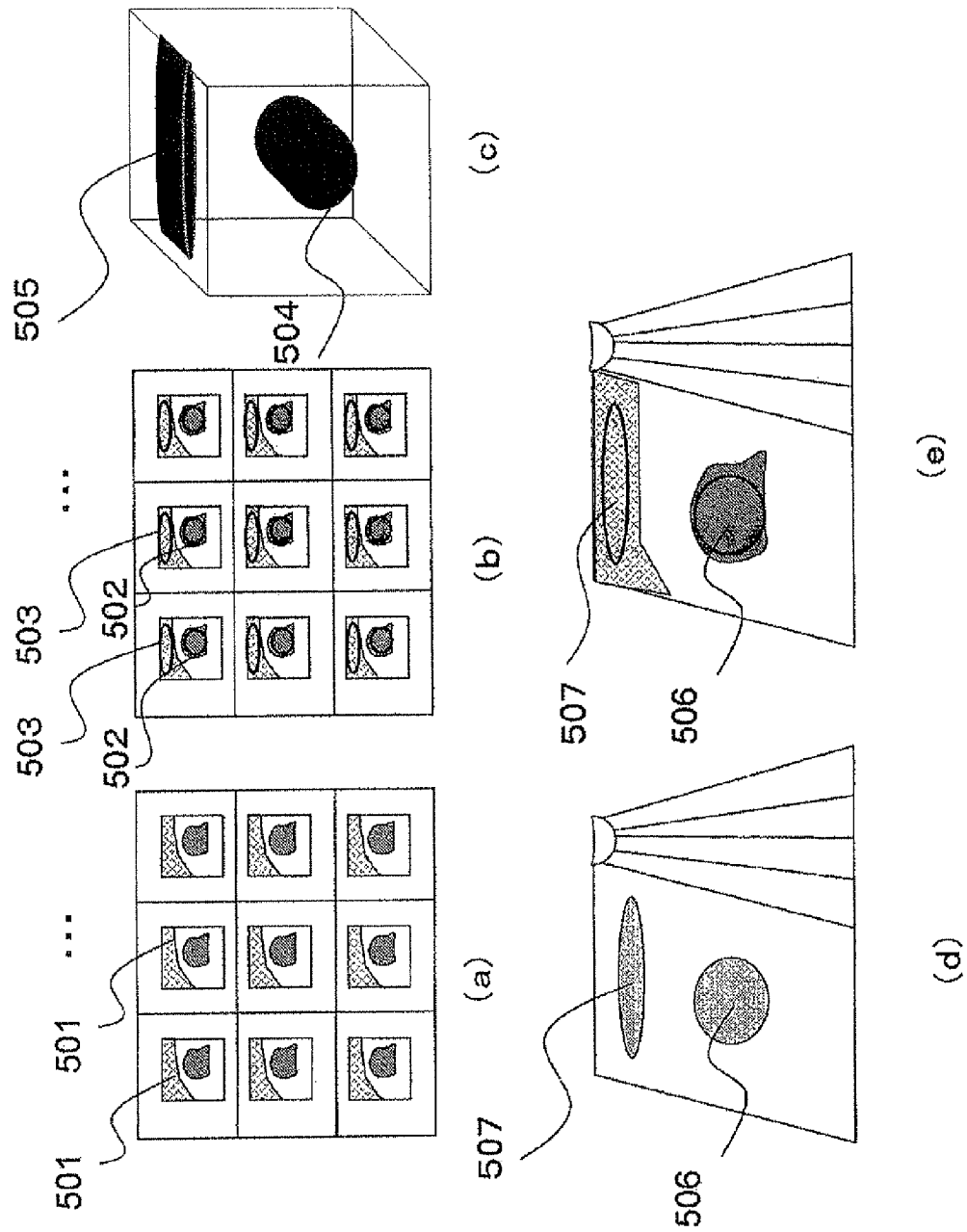
FIG. 5 is a view showing the concept of processing for calculating the three-dimensional distortion ratio of the elastic information in a third example.

FIG. 5 is a view showing the concept of processing for calculating the three-dimensional elastic ratio (three-dimensional distortion ratio) of the elastic information in the third example. First, as shown in FIG. 5(a), an elastic multi-slice image 501 is displayed on the image display device 13. The elastic multi-slice image is one of methods for three-dimensional observation, and is advantageous in that different cross sections at the arbitrary cutting angle in the XYZ coordinate system can be displayed simultaneously on plural divided screens.

As shown in FIG. 5(b), an operator sets two three-dimensional regions of interest 502 and 503 on the elastic multi-slice image 501 through the input interface unit 43. Hereinafter, the two three-dimensional regions of interest 502 and 503 are appropriately called ROI1 and ROI2. By setting the ROI1 and the ROI2 on each elastic multi-slice image 501 as described above, the size corresponding to the slice surface can be easily set by adjusting the ROI in the case of a tumor whose diameter changes largely in the Y direction, for example.

Then, as shown in FIG. 5(c), the three-dimensional regions of interest 502 and 503 are made as data, that is, as mask information items 504 and 505 of XYZ data. That is, as shown in FIG. 5(b), the ROI information set on the elastic multi-slice image 501 is two-dimensional information visually, but is information to be managed as XYZ coordinates. Accordingly, the ROI information set on the elastic multi-slice image 501 can be easily made as data, that is, as mask information of XYZ data shown in FIG. 5(c). Then, as shown in FIG. 5(d), the mask information items 504 and 505 are coordinate-transformed from the Cartesian coordinate system of XYZ to the polar coordinate system of RΘΦ by the coordinate transformation unit 50. As a result, ROI mask data sets 506 and 507 in the RΘΦ coordinate system are created.

The three-dimensional distortion ratio measuring unit 52 can refer to the elastic information (distortion) of the three-dimensional region of interest, which is set in the XYZ coordinate system from the elastic information volume data in the RΘΦ coordinate system, by ON/OFF control of the ROI mask data sets 506 and 507, as shown in FIG. 5(e). As a result, a three-dimensional elastic ratio is calculated on the basis of the elastic information of the ROI mask data 506 and the elastic information of the ROI mask data 507 converted to the RΘΦ coordinate system. The method of calculating the three-dimensional elastic ratio is the same as that in the first example.

In this example, setting the ROI1 and the ROI2 for measurement using an elastic multi-slice image as positional information has been described. However, the invention is not limited to this, and the ROI1 and the ROI2 for measurement may also be set on a tomographic multi-slice image or on a composite multi-slice image in which a tomographic image and an elastic image overlap each other.

Fourth Example

A fourth example of the ultrasonic diagnostic apparatus of the present embodiment will be described. This example is different from the first example in that first and second three-dimensional regions of interest converted to the RΘΦ coordinate system by the coordinate transformation unit 50 are displayed on the image display device 13 in the RΘΦ coordinate system so that at least one of the first and second three-dimensional regions of interest displayed in the RΘΦ coordinate system is adjustable on the image. Accordingly, explanation regarding a portion overlapping the first embodiment will be omitted.

Figure 6:
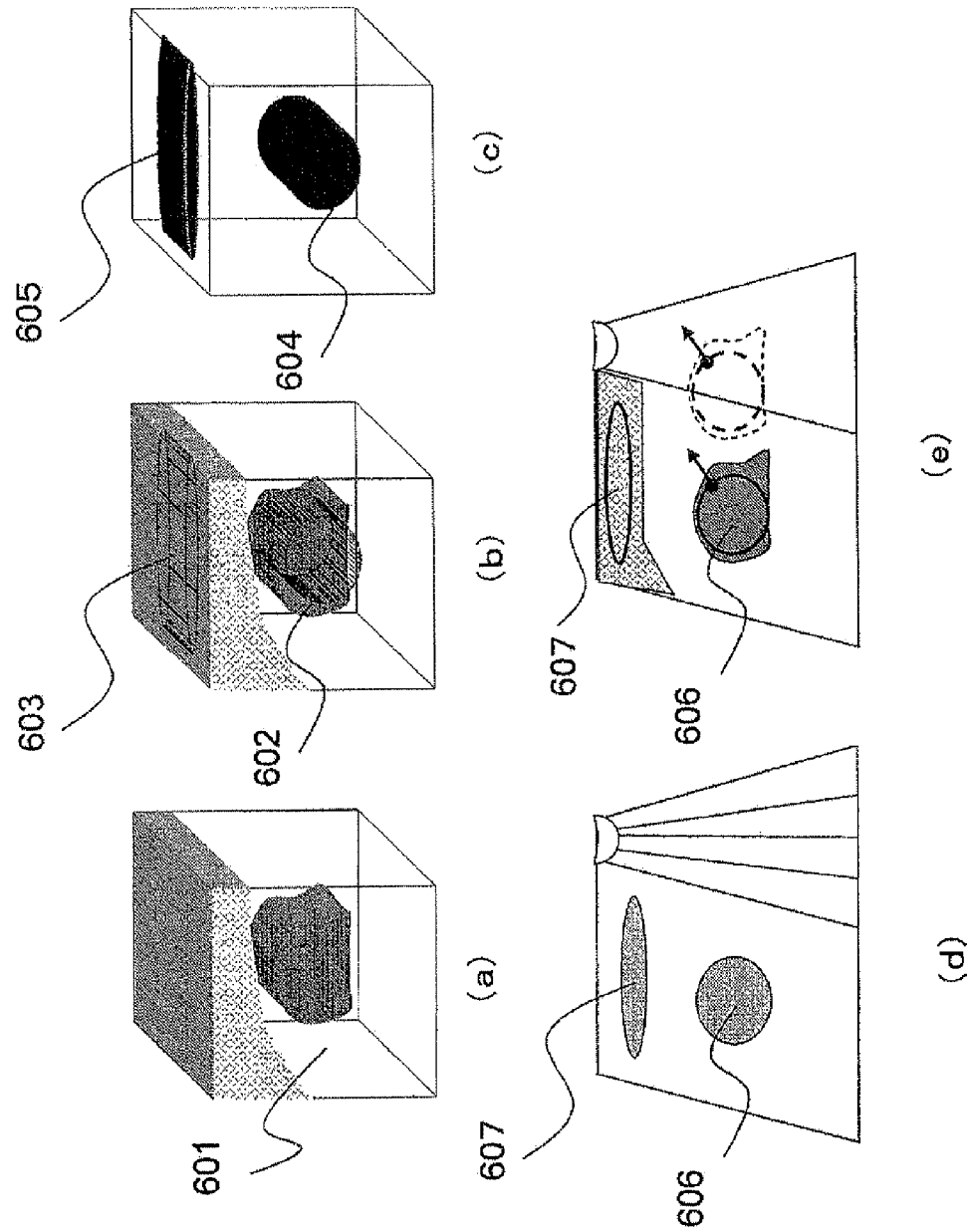
FIG. 6 is a view showing the concept of processing for calculating the three-dimensional distortion ratio of the elastic information in a fourth example.
Figure 7:
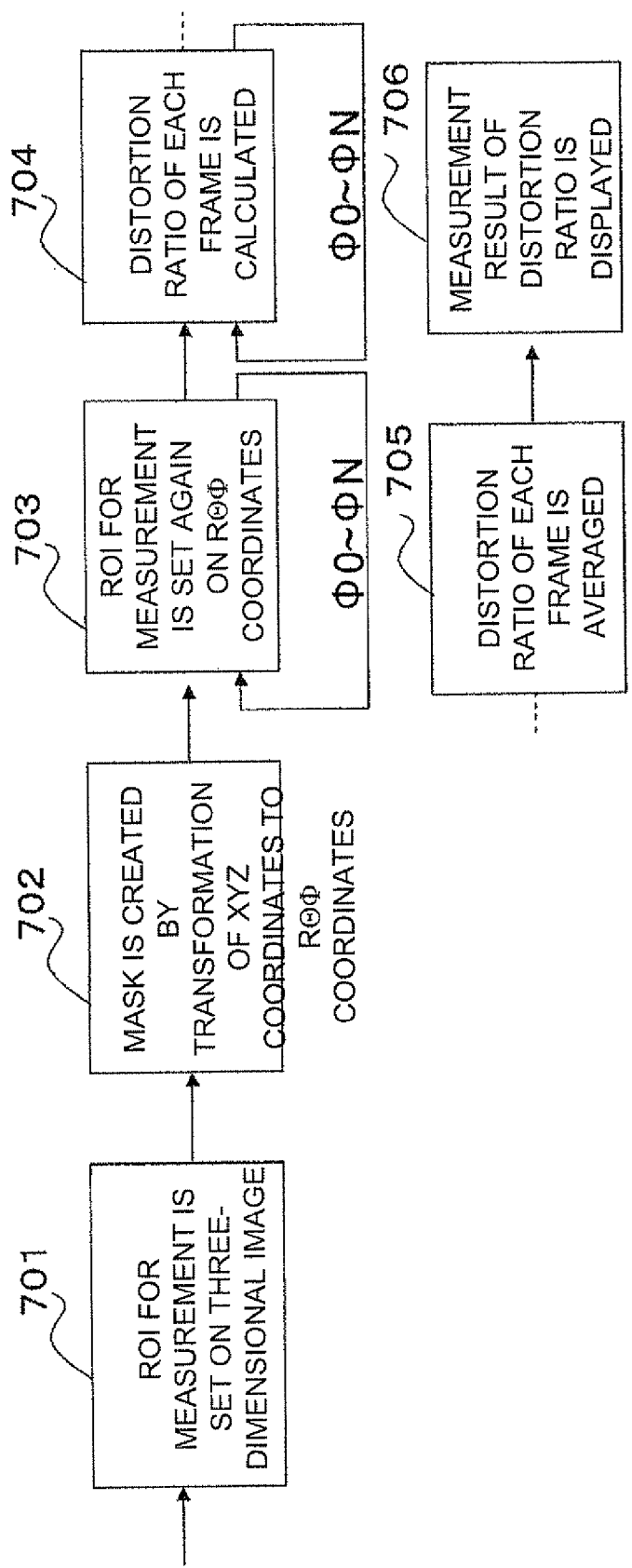
FIG. 7 is a flow chart of the processing in the fourth example.

FIG. 6 is a view showing the concept of processing for calculating the three-dimensional distortion ratio of the elastic information in the fourth example. FIG. 7 is a flow chart of the processing in the fourth example. First, as shown in FIG. 6(a), an elastic rendering image 601 is displayed on the image display device 13. As shown in FIGS. 6(b) and 7, an operator sets two three-dimensional regions of interest 602 and 603 on the elastic rendering image 601 through the input interface unit 43 so as to be transparent or overwritten (701 in FIG. 7). Hereinafter, the two three-dimensional regions of interest 602 and 603 are appropriately called ROI1 and ROI2.

Then, as shown in FIG. 6(c), the three-dimensional regions of interest 602 and 603 are made as data, that is, as mask information items 604 and 605 of XYZ data. Then, as shown in FIG. 6(d), the mask information items 604 and 605 are coordinate-transformed from the Cartesian coordinate system of XYZ to the polar coordinate system of RΘΦ by the coordinate transformation unit 50. As a result, ROI mask data 606 and 607 in the RΘΦ coordinate system are created (702 in FIG. 7).

As shown in FIG. 6(e), the operator adjusts the ROI mask data 606 and 607 converted to the RRΘΦ coordinate system on the image in the polar coordinate system of RΘΦ while referring to the image display device 13 (703 in FIG. 7). The three-dimensional distortion ratio measuring unit 52 can refer to the elastic information (distortion) of the three-dimensional region of interest, which is set in the XYZ coordinate system from the elastic information volume data in the RΘΦ coordinate system, by ON/OFF control of the adjusted ROI mask data 606 and 607, as shown in FIG. 6(e). As a result, a three-dimensional elastic ratio is calculated on the basis of the elastic information of the ROI mask data 606 and the elastic information of the ROI mask data 607 adjusted by conversion to the RΘΦ coordinate system.

Specifically, by calculating the average distortion in each frame in each of the ROI1 and the ROI2, the ratio of distortion between the ROI1 and the ROI2 is calculated (704 in FIG. 7). As a result, it is possible to calculate the distortion ratio for each frame. Finally, a three-dimensional distortion ratio is calculated by averaging of the value calculated for each frame (705 in FIG. 7), and the calculated three-dimensional distortion ratio is displayed on the image display device 13 (706 in FIG. 7).

Fifth Example

A fifth example of the ultrasonic diagnostic apparatus of the present embodiment will be described. This example is different from the first example in that the three-dimensional distortion ratio measuring unit 52 detects sections with the same pressure state in the first and second regions of interest on the basis of a temporal change in the pressure state of tissue of an object in the RΘΦ coordinate system and calculates a three-dimensional elastic ratio on the basis of the elastic information of the detected sections with the same pressure state. Accordingly, explanation regarding a portion overlapping the first embodiment will be omitted. The three-dimensional distortion ratio measuring unit 52 (three-dimensional elastic ratio measuring unit) calculates a three-dimensional elastic ratio between the elastic information of a region corresponding to the first three-dimensional region of interest and the elastic information of a region corresponding to the second three-dimensional region of interest in plural elastic frame data with the same pressure state of tissue of the object.

In the methods shown in the first to fourth examples, two ROIs need to be set at the same φ position in the RΘΦ coordinate system in order to calculate the distortion ratio along the stress plane. This is because stress changes with pressure and accordingly, tissue distortion occurring due to pressure changes largely. This example is an example where a three-dimensional elastic ratio is calculated when two ROIs are not set as the same φ position in the RΘΦ coordinate system.

FIG. 8 is a view showing the concept of processing for calculating the three-dimensional distortion ratio of the elastic information in the fifth example. FIG. 8(a) shows a cross-sectional image 801 of the YZ plane (short axis direction) in the XYZ coordinate system. In addition, a pressure graph creating unit 54 shown in FIG. 1 receives the output data from the displacement measuring unit 30, the elastic information calculating unit 32, or the pressure measuring unit 45 and creates a pressure graph 802 shown in FIG. 8(b).

By generating the pressure graph 802, the three-dimensional distortion ratio measuring unit 52 can grasp a temporal change in displacement, distortion, or stress along the φ direction. The three-dimensional distortion ratio measuring unit 52 detects sections (similar sections 803) with the same pressure state in the ROI1 and the ROI2 by performing a correlation operation on the pressure graphs of the ROI1 and the ROI2.

Then, the three-dimensional distortion ratio measuring unit 52 selects the detected two similar sections 803, calculates the average distortion of each section, and calculates a ratio of the average distortion. The method of calculating the three-dimensional elastic ratio is the same as that in the first example.

Accordingly, it becomes possible to compare the distortion ratio at the same pressure level. In addition, for example, when the position of a reference object (soft object with little individual difference, such as fat) and the position of a tumor (lesion which forms a benign and malignant tumor image) are different in the short axis direction, it is difficult to compare them in the same frames. Regarding this point, according to this example, the distortion ratio in sections with the same pressure state is calculated even if two ROIs are not set at the same φ position in the RΘΦ coordinate system. As a result, the hardness or softness of a diagnostic part can be accurately quantified.

Sixth Example

A sixth example of the ultrasonic diagnostic apparatus of the present embodiment will be described. The present example is different from the first example in that the three-dimensional distortion ratio measuring unit 52 detects a section, in which pressure is applied to tissue of an object, and a section, in which no pressure is applied to tissue of the object, on the basis of a temporal change in the pressure state of tissue of the object in the RΘΦ coordinate system and calculates a three-dimensional elastic ratio on the basis of the elastic information of only one of the section in which pressure is applied and the section in which no pressure is applied in first and second three-dimensional regions of interest. Accordingly, explanation regarding a portion overlapping the first embodiment will be omitted. The three-dimensional distortion ratio measuring unit 52 (three-dimensional elastic ratio measuring unit) detects a section, in which pressure is applied to tissue of an object, and a section, in which no pressure is applied to tissue of the object, on the basis of a temporal change in the pressure state of tissue of the object and calculates a three-dimensional elastic ratio on the basis of the elastic information of only one of the section in which pressure is applied and the section in which no pressure is applied in the first and second three-dimensional regions of interest.

Figure 9:
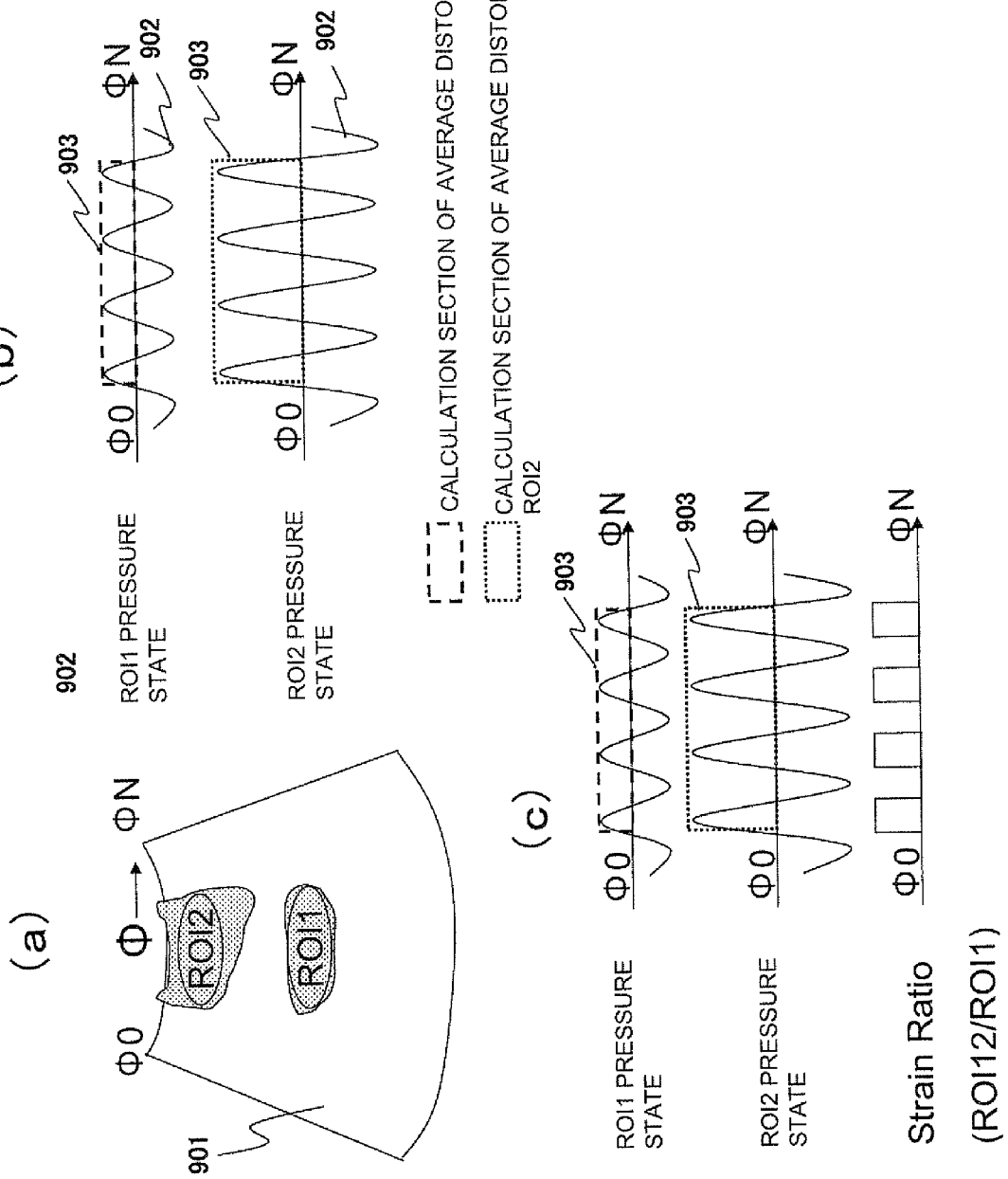
FIG. 9 is a view showing the concept of processing for calculating the three-dimensional distortion ratio of the elastic information in a sixth example.

FIG. 9 is a view showing the concept of processing for calculating the three-dimensional distortion ratio of the elastic information in the sixth example. FIG. 9(a) shows a cross-sectional image 901 of the YZ plane (short axis direction) in the XYZ coordinate system. In addition, the pressure graph creating unit 54 shown in FIG. 1 receives the output data from the displacement measuring unit 30, the elastic information calculating unit 32, or the pressure measuring unit 45 and creates a pressure graph 902 shown in FIG. 9(b).

By generating the pressure graph 902, the three-dimensional distortion ratio measuring unit 52 can grasp a temporal change in displacement, distortion, or stress along the φ direction. The three-dimensional distortion ratio measuring unit 52 detects a section, in which pressure is applied to tissue of the object, and a section, in which no pressure is applied to tissue of the object, on the basis of a temporal change (change in the φ direction) in the pressure state in the ROI1 and the ROI2 shown in the pressure graph 902. Here, it is assumed that the section in which pressure is applied to tissue of the object has been detected as a pressure section 903. As shown in FIG. 9(c), the three-dimensional distortion ratio measuring unit 52 calculates the average distortion in the pressure section 903 of the ROI1 and the ROI2 and calculates the ratio. The method of calculating the three-dimensional elastic ratio is the same as that in the first example.

According to this example, degradation of the measured value by image shift caused by tissue displacement can be reduced by making the direction of pressure the same. Therefore, it is possible to calculate the three-dimensional distortion ratio with high precision. In addition, although an example of calculating the average distortion in the section where pressure is applied is shown in this example, the invention is not limited to this, and it is also possible to calculate the average distortion in a section where no pressure is applied.

Seventh Example

A seventh example of the ultrasonic diagnostic apparatus of the present embodiment will be described. This example is different from the first example in that the three-dimensional distortion ratio measuring unit 52 calculates an integrated value of the elastic information in first and second three-dimensional regions of interest on the basis of a temporal change in the pressure state of tissue of an object in the RΘΦ coordinate system, estimates a distance between the tissue of the object and the pressure start position on the basis of the calculated integrated value, and calculates a three-dimensional elastic ratio on the basis of the elastic information of a section with the estimated distance which is larger or smaller than a distance threshold value set in advance. Accordingly, explanation regarding a portion overlapping the first embodiment will be omitted.

Figure 10:
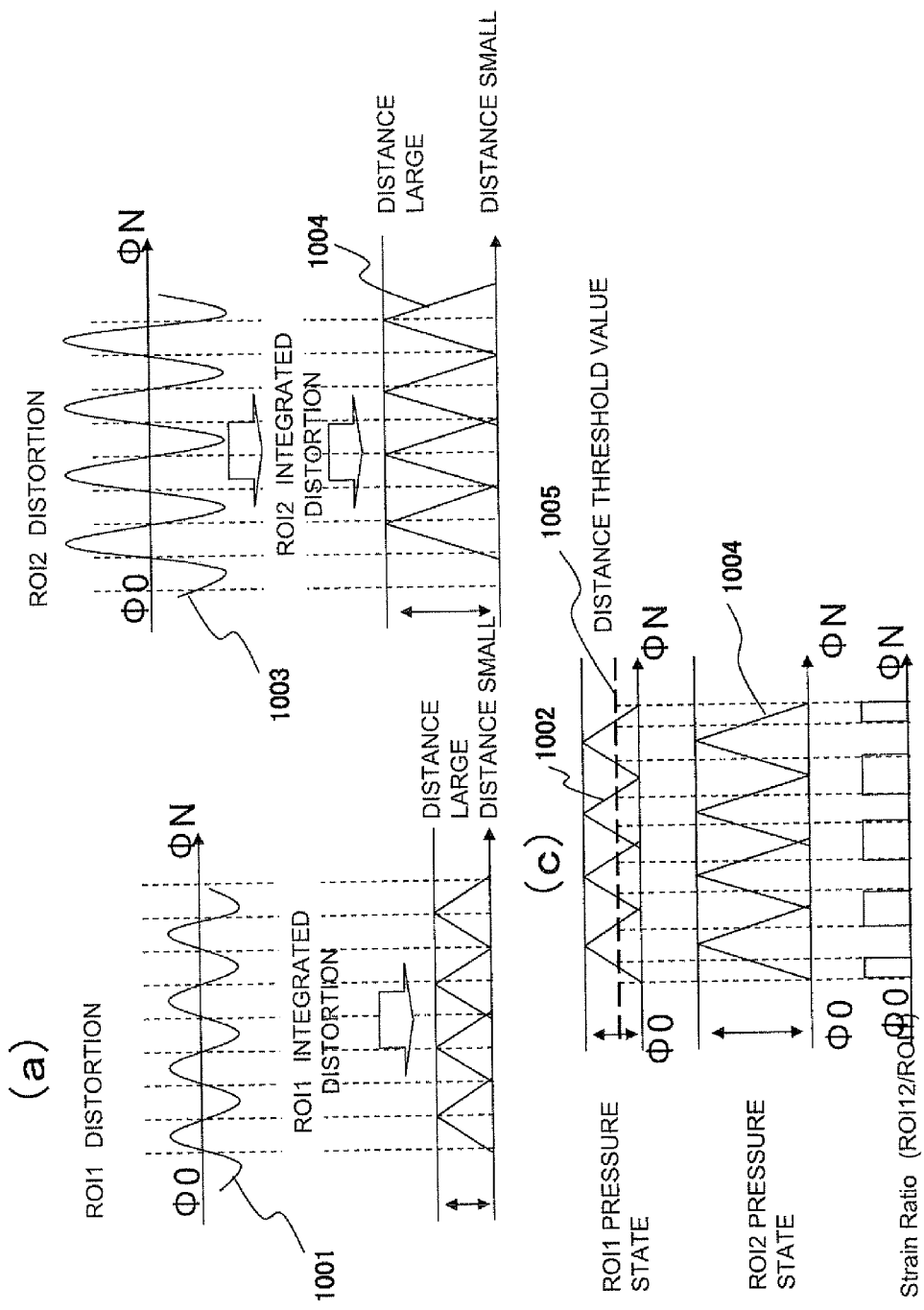
FIG. 10 is a view showing the concept of processing for calculating the three-dimensional distortion ratio of the elastic information in a seventh example.

FIG. 10 is a view showing the concept of processing for calculating the three-dimensional distortion ratio of the elastic information in the seventh example. First, the pressure graph creating unit 54 shown in FIG. 1 receives the output data from the displacement measuring unit 30, the elastic information calculating unit 32, or the pressure measuring unit 45 and creates a pressure graph 1001 in the ROI1 as shown in the upper part of FIG. 10(a). In addition, as shown in the lower part of FIG. 10(a), pressure information of the pressure graph 1001 in the ROI1 is integrated to generate an integration graph 1002.

On the other hand, also in the ROI2, the pressure graph creating unit 54 generates an integration graph 1004 by integrating the pressure information of the pressure graph 1003 in the ROI2, as shown in FIG. 10(b).

The three-dimensional distortion ratio measuring unit 52 can estimate a moving distance of an ultrasonic probe from the initial pressure position by referring to the integration graphs 1002 and 1004. As shown in FIG. 10(c), the three-dimensional distortion ratio measuring unit 52 calculates the average distortion of the ROI1 and the ROI2 in a section in which the integrated value of the integration graph 1002 is smaller than the distance threshold value 1005, that is, in a section in which the amount of movement of the probe from the initial pressure position is small, and calculates the ratio. The method of calculating the three-dimensional elastic ratio is the same as that in the first example.

According to this example, since a ratio of the ROI1 and the ROI2 with the same level of pressure position can be calculated, it is possible to reduce the degradation of the measured value. As a result, it is possible to calculate the distortion ratio with high precision. In addition, although an example of calculating the average distortion in the section where the integrated value of the integration graph is larger than the distance threshold value is shown in this example, the invention is not limited to this, and it is also possible to calculate the average distortion in a section where the integrated value of the integration graph is smaller than the distance threshold value, that is, in a section where the amount of movement of the probe from the initial pressure position is large.

Eighth Example

An eighth example of the ultrasonic diagnostic apparatus of the present embodiment will be described. The present example is different from the first example in that the three-dimensional distortion ratio measuring unit 52 detects a section, in which pressure is applied to tissue of an object, and a section, in which no pressure is applied to tissue of the object, on the basis of a temporal change in the pressure state of tissue of the object in the RΘΦ coordinate system and calculates a three-dimensional elastic ratio on the basis of the elastic information of the peak of the section in which pressure is applied or the section in which no pressure is applied in first and second three-dimensional regions of interest. Accordingly, explanation regarding a portion overlapping the first embodiment will be omitted.

Figure 11:
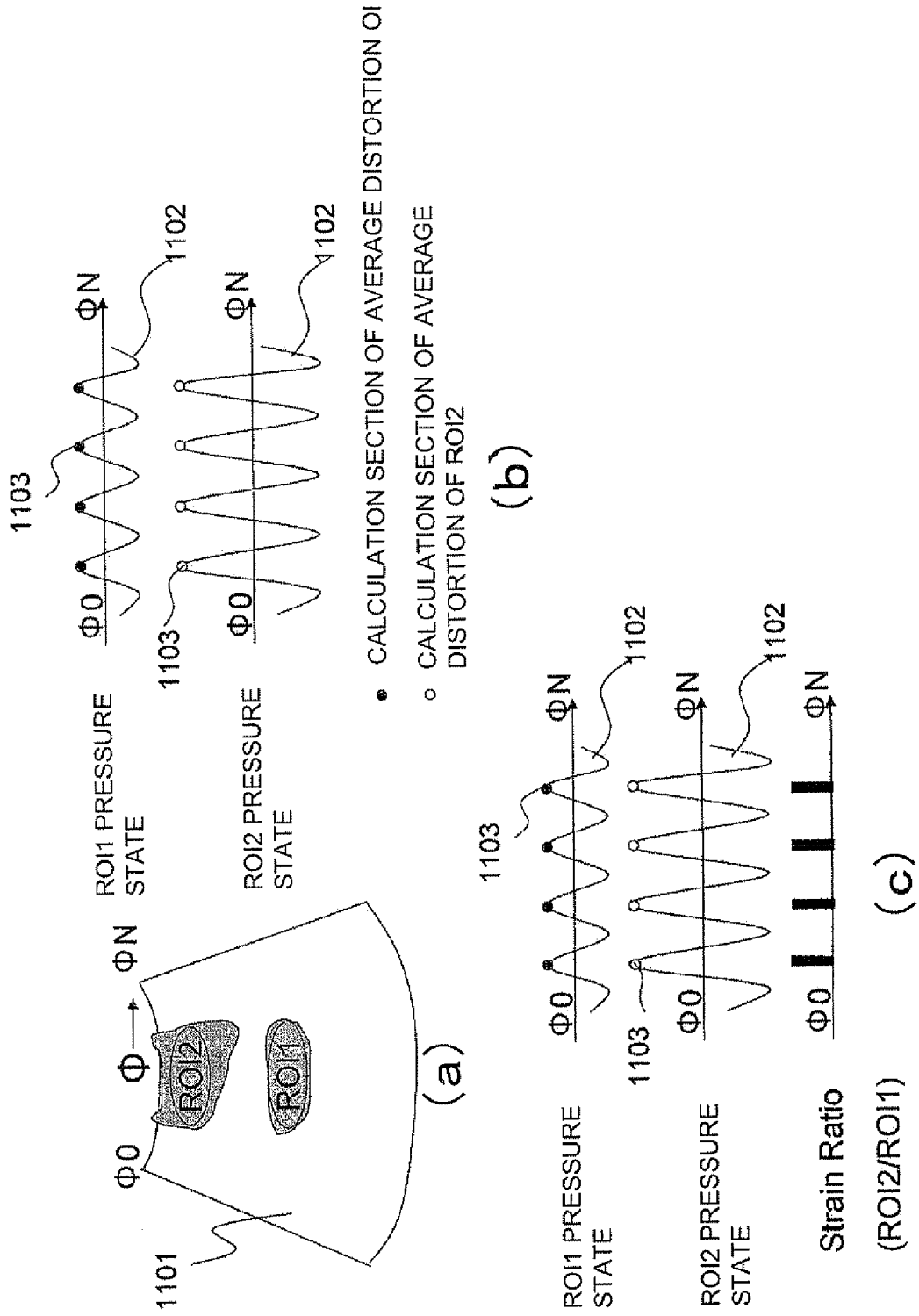
FIG. 11 is a view showing the concept of processing for calculating the three-dimensional distortion ratio of the elastic information in an eighth example.

FIG. 11 is a view showing the concept of processing for calculating the three-dimensional distortion ratio of the elastic information in the eighth example. FIG. 11(a) shows a cross-sectional image 1101 of the YZ plane (short axis direction) in the XYZ coordinate system. In addition, the pressure graph creating unit 54 shown in FIG. 1 receives the output data from the displacement measuring unit 30, the elastic information calculating unit 32, or the pressure measuring unit 45 and creates a pressure graph 1102 shown in FIG. 9(b).

By generating the pressure graph 1102, the three-dimensional distortion ratio measuring unit 52 can grasp a temporal change in displacement, distortion, or stress along the φ direction. The three-dimensional distortion ratio measuring unit 52 detects a peak 1103 of a section, in which pressure is applied to tissue of the object, and a section, in which no pressure is applied to tissue of the object, on the basis of a temporal change (change in the φ direction) in the pressure state in the ROI1 and the ROI2 shown in the pressure graph 1102. Here, it is assumed that a time phase with a peak pressure state is selected in the section in which pressure is applied to tissue of the object. As shown in FIG. 11(c), the three-dimensional distortion ratio measuring unit 52 calculates the average distortion in the peak 1103 of each of the ROI1 and the ROI2 and calculates the ratio. The method of calculating the three-dimensional elastic ratio is the same as that in the first example.

According to this example, there is an advantage in that the number of measurement points, at which the elastic information (distortion) is referred to, is reduced. For example, the three-dimensional distortion ratio can be measured more accurately than in the sixth example described above. In addition, although an example of calculating the average distortion at the peak of the pressure state in the section where pressure is applied is shown in this example, the invention is not limited to this, and it is also possible to calculate the average distortion at the peak of the pressure state in a section where no pressure is applied. In addition, without being limited to the peak of the pressure state, it is also possible to select the calculation position of the average distortion arbitrarily through the input interface unit 43, for example, it is possible to select the position at which the pressure state is 0.

Ninth Example

A ninth example of the ultrasonic diagnostic apparatus of the present embodiment will be described. This example is different from the first example in that the three-dimensional distortion ratio measuring unit 52 calculates a three-dimensional elastic ratio on the basis of two-dimensional elastic ratios in plural remaining tomographic planes after excluding a two-dimensional elastic ratio, which deviates from the elastic ratio threshold value range set in advance, among two-dimensional elastic ratios calculated in plural tomographic planes (elastic frame data) with the same pressure states of tissue of an object. Accordingly, explanation regarding a portion overlapping the first embodiment will be omitted.

Figure 12:
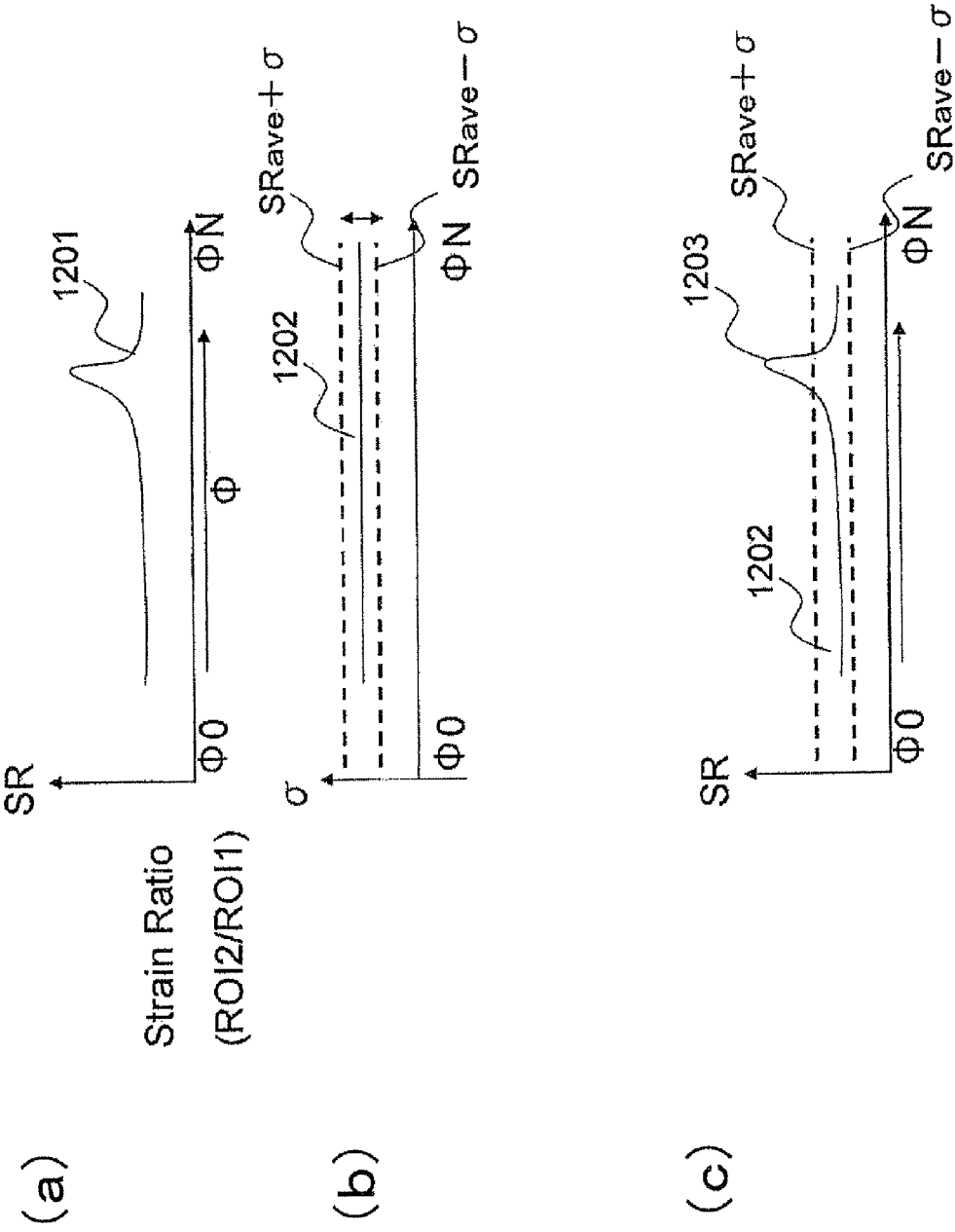
FIG. 12 is a view showing the concept of processing for calculating the three-dimensional distortion ratio of the elastic information in a ninth example.

FIG. 12 is a view showing the concept of processing for calculating the three-dimensional distortion ratio of the elastic information in the ninth example. FIG. 12(*a*) is an example of a two-dimensional distortion ratio graph with a horizontal axis indicating a change in the φ direction and a vertical axis indicating the distortion ratio (SR). As shown in a two-dimensional distortion ratio graph 1201 in FIG. 12(*a*), when calculating a three-dimensional distortion ratio, abnormal values may occur due to noise or the like in the φ direction, and this may degrade the quantification. Therefore, the three-dimensional distortion ratio measuring unit 52 excludes a two-dimensional elastic ratio, which deviates from the elastic ratio threshold value range set in advance, among the two-dimensional elastic ratios calculated along the φ direction.

Specifically, in order to set the elastic ratio threshold value range, average distortion (SRave) and a deviation (σ) of the average distortion are calculated by the following Expressions 23 and 24. As shown in FIG. 12(*b*), an elastic ratio threshold value range 1202 shown in the range of SRave±σ is determined.

$$SRave = \frac{\sum_{\phi=\phi0}^{\phi N} SR(\phi)}{N_\phi}$$ [Expression 23]

$$\sigma = \sqrt{\frac{\sum_{\phi=\phi0}^{\phi N} (SR(\phi) - SRave)^2}{N}}$$ [Expression 24]

Then, as shown in the following Expression 25, the three-dimensional distortion ratio measuring unit 52 selects only two-dimensional distortion ratios in the range of SRave±σ in the φ direction and performs averaging of the selected two-dimensional distortion ratios to calculate a three-dimensional distortion ratio. In other words, as shown in FIG. 12(*c*), a two-dimensional distortion ratio 1203 which is larger than SRave±σ is excluded, as noise, from the calculation for calculating the three-dimensional distortion ratio. According to this example, since the three-dimensional distortion ratio is calculated by adopting only values within the elastic ratio threshold value range, it is possible to calculate an appropriate three-dimensional distortion ratio after removing the influence of noise.

$$SRfinal = \frac{\sum_{\phi=\phi0}^{\phi N} SR(\phi)}{N} (SRave - \sigma < SR(\phi) < SRave + \sigma)$$ [Expression 25]

Tenth Example

A tenth example of the ultrasonic diagnostic apparatus of the present embodiment will be described. This example is different from the first example in that when one slice image cut from the elastic volume data converted to the XYZ coordinate system is generated and displayed on the image display device 13 and plural regions of interest are set on the displayed one slice image in the XYZ coordinate system through the input interface unit 43, the elastic slice image generating unit 48 detects a corresponding region on plural slice images in a direction perpendicular to the one slice image for each of the plurality of regions of interest which has been set and generates first and second three-dimensional regions of interest automatically on the basis of the set regions of interest and the detected plural regions. Accordingly, explanation regarding a portion overlapping the first embodiment will be omitted.

Figure 13:
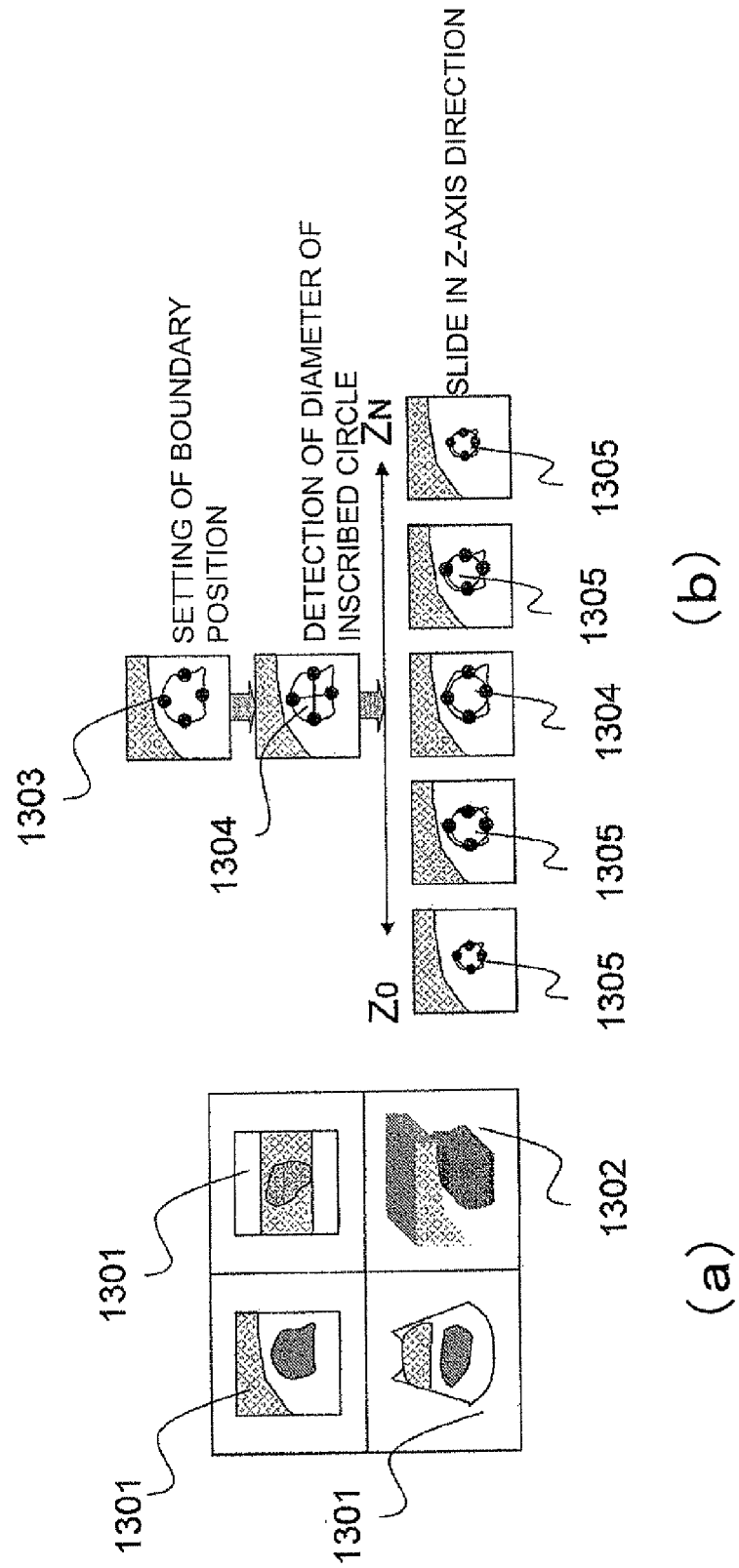
FIG. 13 is a view showing the concept of processing for automatic setting of ROI1 and ROI2 in a tenth example.

FIG. 13 is a view showing the concept of processing for automatic setting of ROI1 and ROI2 in the tenth example. First, as shown in FIG. 13(*a*), an MPR image 1301 and an elastic rendering image 1302 are displayed on the image display device 13. Specifically, elastic images of the XY plane, the YZ plane, and the XZ plane in the XYZ coordinate system are displayed as the MPR image 1301 in upper left, lower left, and upper right regions of four divided regions of the screen, and the elastic rendering image 1302 is displayed in a lower right region of the screen. However, the elastic rendering image 1302 may not be displayed.

For example, an operator selects an arbitrary slice surface of the XY cross section in the MPR image 1301 and selects several points of a boundary portion of a region of interest, such as a tumor, as selection points 1303, as shown in FIG. 13(*b*) (in this example, four points). Then, an inscribed circle according to the selected diameter which connects the selection points 1303 to each other is set as a region of interest 1304. Then, the boundary set in the region of interest 1304 is detected as a detection region 1305 on each cross section sliding in the Z direction using a signal tracking method represented by a tissue tracking method. By connecting the region of interest 1304 and the plural detection regions 1305 in the Z-axis direction, a three-dimensional ROI is automatically generated.

According to this example, a three-dimensional ROI is automatically generated lust by setting a region of interest on one cross section by the operator. Therefore, since the apparatus is user-friendly, it is possible to improve the diagnostic efficiency. In addition, although an example of setting one ROI is shown in this example for convenience of description, plural ROIs (for example, two ROIs) are set in practice in order to calculate a three-dimensional distortion ratio. Processing after the three-dimensional ROI is set is the same as that in the first example.

Eleventh Example

An eleventh example of the ultrasonic diagnostic apparatus of the present embodiment will be described. This example is different from the first example in that when setting two regions of interest on elastic MPR images, guide display is performed on the basis of the position and size of a region of interest set first so that a region of interest is set at the appropriate position when setting a region of interest next. Accordingly, explanation regarding a portion overlapping the first embodiment will be omitted.

Figure 14:
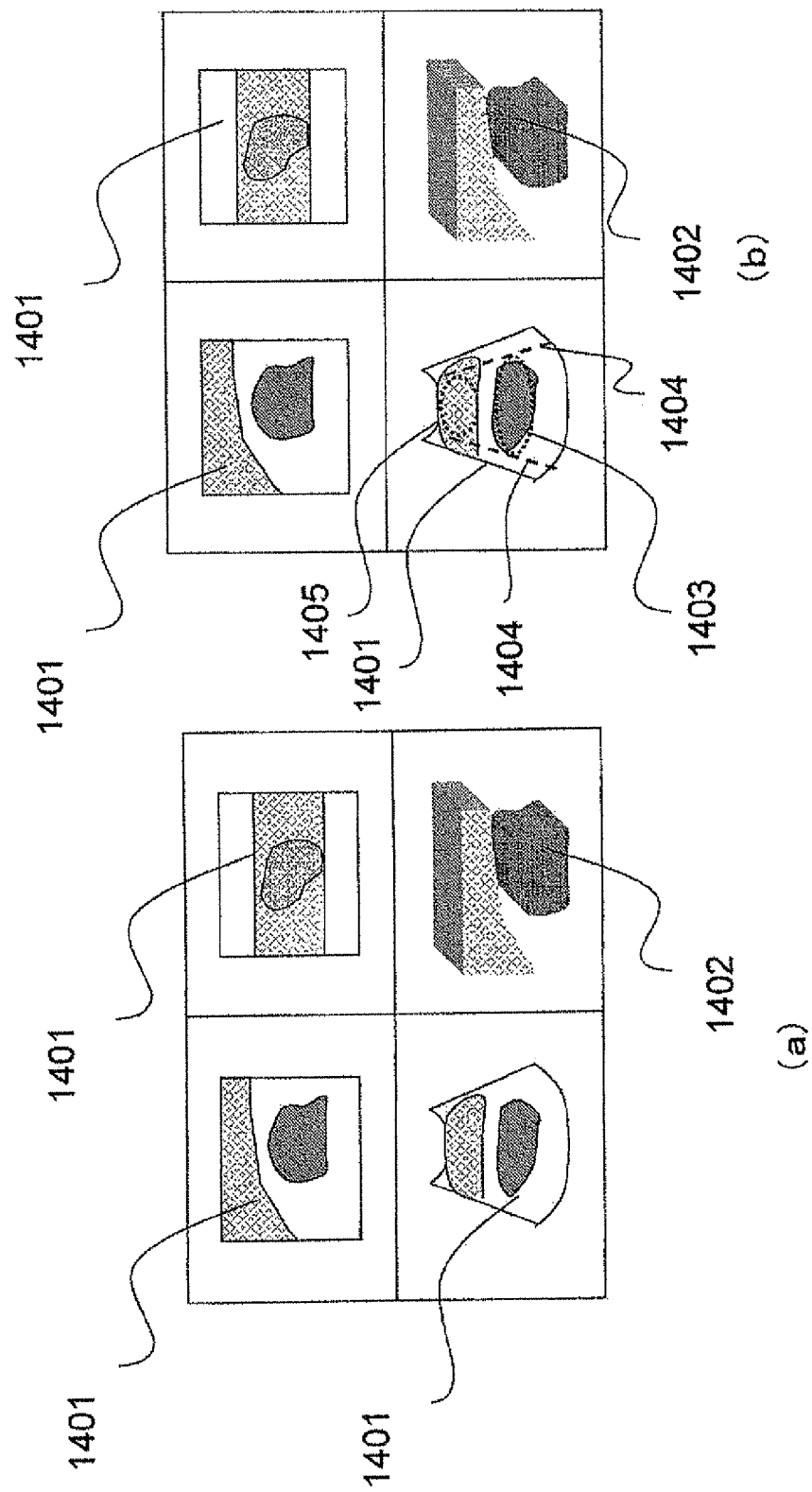
FIG. 14 is a view showing an example of guide display when setting an ROT in an eleventh example.

FIG. 14 is a view showing an example of guide display when setting an ROI in the eleventh example. First, as shown in FIG. 14(*a*), an MPR image 1401 and an elastic rendering image 1402 are displayed on the image display device 13. Specifically, elastic images of the XY plane, the YZ plane, and the XZ plane in the XYZ coordinate system are displayed as the MPR image 1401 in upper left, lower left, and upper right regions of four divided regions of the screen, and the elastic rendering image 1402 is displayed in a lower right region of the screen. However, the elastic rendering image 1402 may not be displayed.

Incidentally, in order to calculate a three-dimensional distortion ratio, it is desirable to set two ROIs on the same frame. Preferably, ROIs set when performing three-dimensional measurement are set so as to be a pair for the Z coordinate (time direction). Therefore, as shown in FIG. 14(b), when setting a region of interest on the YZ plane of the MPR image 1401, two guide lines 1404 are displayed by extending tangential lines of both ends in the horizontal direction of an ROI (first ROI 1403), which is set or designated first, along the scan frame line.

By referring to the two guide lines 1404, the operator can grasp that it is desirable to set the next ROI (second ROI 1405) so as to be inserted between the guide lines 1404 and be in contact with the guide lines 1404. Therefore, according to this example, the operator can set easily two regions of interest so as to be a pair for the Z coordinate (time direction). As a result, the ratio of three-dimensional elastic information can be appropriately calculated, and the apparatus is user-friendly.

In addition, the second ROI 1405 may also be set automatically with the angle of the guide line 1404 as a reference. Moreover, in order to change the set ROIs, the size of the other ROI may be automatically changed simultaneously with change of one of the first and second ROIs. In addition, as shown in FIG. 14(b), it is possible to reduce the effort of the operator by setting the guide line 1404 on the YZ plane (time direction) along the contour of a tumor.

DESCRIPTION OF REFERENCE NUMERALS AND SIGNS

1: object
2: ultrasonic probe
6: phasing addition unit
30: displacement measuring unit
32: elastic information calculating unit
34: elastic image forming unit
39: two-dimensional elastic image storage unit
40: elastic volume data generating unit
41: elastic three-dimensional scan conversion unit
42: elastic volume rendering unit
48: elastic slice image generating unit
44: image system control unit
43: input interface unit
50: coordinate transformation unit
52: three-dimensional distortion ratio measuring unit
100: ultrasonic diagnostic apparatus
201, 601, 1302, 1402: elastic rendering image
202, 203, 402, 403, 502, 503, 602, 603: three-dimensional region of interest
401, 1301, 1401: MPR image
501: elastic multi-slice image
802, 902, 1001, 1003, 1102: pressure graph
803: similar section
903: pressure section
1002, 1004: integration graph
1005: distance threshold value
1103: peak
1201: two-dimensional distortion ratio graph
1202: elastic ratio threshold value range
1303: selection point
1304: regions of interest
1305: detection region

The invention claimed is:

1. An ultrasonic diagnostic apparatus comprising:
an ultrasonic probe which transmits ultrasonic waves to an object to be examined and receives reflected echo signals from the object; and
an ultrasonic diagnostic system comprising circuitry, memory and a display, which operate to:
provide electrical signals to the ultrasonic probe that transmits the ultrasonic waves to the object;
amplify the reflected echo signals received by the ultrasonic probe at a predetermined gain and generate radio-frequency (RF) signals;
obtain RF signal frame data from the generated RF signals;
store the obtained RF signal frame data;
slide on a scan plane of the ultrasonic probe by motor control;
construct a two-dimensional tomographic image based on the stored RF signal frame data;
measure displacement from plural sets of the stored RF signal frame data;
generate tomographic volume data by performing three-dimensional coordinate conversion based on a position of the constructed two-dimensional tomographic image;
collect the plural sets of elastic volume data obtained by sliding on the scan plane of the ultrasonic wave to be transmitted to the object in the direction which intersects with the scan plane so as to generate elastic volume data;
generate elastic frame data by calculating elastic information indicating the hardness or softness based on the reflected echo signal measured by the ultrasonic probe and generate elastic volume data based on plural sets of elastic frame data;
display at least one of elastic slice images of a plurality of cross sections and an elastic rendering image generated based on the elastic volume data;
set a plurality of three-dimensional regions of interest through at least one of the displayed elastic slice images of the plurality of cross sections and the displayed elastic rendering image; and
calculate a three-dimensional elastic ratio between the elastic information in a set first three-dimensional region of interest and the elastic information in a set second three-dimensional region of interest, the calculated three-dimensional elastic ratio being displayed on the display;
calculate a two-dimensional elastic ratio between elastic information of a region corresponding to the first three-dimensional region of interest and elastic information of a region corresponding to the second three-dimensional region of interest in each of the plural sets of elastic frame data of the elastic rendering image; and
calculate the three-dimensional elastic ratio based on the two-dimensional elastic ratio in each of the plural sets of the elastic frame data.

2. The ultrasonic diagnostic apparatus according to claim 1,
wherein the ultrasonic diagnostic system further operates to calculate the three-dimensional elastic ratio by averaging the two-dimensional elastic ratio calculated in each set of the elastic frame data.

3. The ultrasonic diagnostic apparatus according to claim 1, wherein the ultrasonic diagnostic system further operates to calculate the three-dimensional elastic ratio between elastic information of a region corresponding to the first three-dimensional region of interest and elastic information of a region corresponding to the second three-dimensional region of interest in the plurality of elastic frame data sets with the same pressure state of tissue of the object.

4. The ultrasonic diagnostic apparatus according to claim 3,
wherein the ultrasonic diagnostic system further operates to detect a section in which pressure is applied to tissue of the object, and a section in which no pressure is applied to the tissue of the object, based on a temporal change in the pressure state of the tissue of the object, and calculate the three-dimensional elastic ratio based on the elastic information of either the section in which pressure is applied or the section in which no pressure is applied in the first and second three-dimensional regions of interest.

5. The ultrasonic diagnostic apparatus according to claim 1,
wherein when the elastic volume data is generated in an RΘΦ coordinate system, the ultrasonic diagnostic system further operates to convert the elastic volume data from the RΘΦ coordinate system to an XYZ coordinate system, generate a multi-planar reconstruction (MPR) image of orthogonal three cross sections of the elastic volume data converted to the XYZ coordinate system, and convert the first and second three-dimensional regions of interest, which are set on the MPR image in the XYZ coordinate system displayed on the display unit, from the XYZ coordinate system to the RΘΦ coordinate system, and
the ultrasonic diagnostic system further operates to calculate the three-dimensional elastic ratio based on the elastic information of the first three-dimensional region of interest and the elastic information of the second three-dimensional region of interest converted to the RΘΦ coordinate system.

6. The ultrasonic diagnostic apparatus according to claim 1,
wherein when the elastic volume data is generated in an RΘΦ coordinate system, the ultrasonic diagnostic system further operates to convert the elastic volume data from the RΘΦ coordinate system to an XYZ coordinate system, generate the elastic rendering image based on the elastic volume data converted to the XYZ coordinate system, and convert the first and second three-dimensional regions of interest, which are set on the elastic rendering image in the XYZ coordinate system displayed on the display unit, from the XYZ coordinate system to the RΘΦ coordinate system, and
the ultrasonic diagnostic system further operates to calculate the three-dimensional elastic ratio based on the elastic information of the first three-dimensional region of interest and the elastic information of the second three-dimensional region of interest converted to the RΘΦ coordinate system.

7. The ultrasonic diagnostic apparatus according to claim 5,
wherein the first and second three-dimensional regions of interest converted to the RΘΦ coordinate system are displayed on the display unit in the RΘΦ coordinate system so that at least one of the first and second three-dimensional regions of interest displayed in the RΘΦ coordinate system is adjustable on an image.

8. The ultrasonic diagnostic apparatus according to claim 5,
wherein the ultrasonic diagnostic system further operates to detect sections with the same pressure state in the first and second regions of interest based on a temporal change in the pressure state of tissue of the object in the RΘΦ coordinate system, and calculate a three-dimensional elastic ratio based on elastic information of the detected sections with the same pressure state.

9. The ultrasonic diagnostic apparatus according to claim 5,
wherein the ultrasonic diagnostic system further operates to calculate an integrated value of the elastic information in the first and second three-dimensional regions of interest based on a temporal change in the pressure state of tissue of the object in the RΘΦ coordinate system, estimate a distance between the tissue of the object and a pressure start position based on the calculated integrated value, and calculate the three-dimensional elastic ratio based on elastic information of a section with the estimated distance which is larger or smaller than a distance threshold value set in advance.

10. The ultrasonic diagnostic apparatus according to claim 5,
wherein the ultrasonic diagnostic system further operates to detect a section in which pressure is applied to tissue of the object, and a section in which no pressure is applied to tissue of the object, based on a temporal change in the pressure state of tissue of the object in the RΘΦ coordinate system, and calculate the three-dimensional elastic ratio based on the elastic information of a peak of the section in which pressure is applied or the section in which no pressure is applied in the first and second three-dimensional regions of interest.

11. The ultrasonic diagnostic apparatus according to claim 1,
wherein the ultrasonic diagnostic system further operates to calculate the three-dimensional elastic ratio based on two-dimensional elastic ratios in a plurality of remaining tomographic planes after excluding a two-dimensional elastic ratio, which deviates from an elastic ratio threshold value range set in advance, among two-dimensional elastic ratios calculated in a plurality of tomographic planes with the same pressure states of tissue of the object.

12. A three-dimensional elastic ratio calculating method comprising:
transmitting an ultrasonic wave to an object to be examined and receiving reflected echo signals from the object; and
providing electrical signals to the ultrasonic probe that transmits the ultrasonic waves to the object;
amplifying the reflected echo signals received by the ultrasonic probe at a predetermined gain and generate radio-frequency (RF) signals;
obtaining RF signal frame data from the generated RF signals;
storing the obtained RF signal frame data;
sliding on a scan plane of the ultrasonic probe by motor control;
constructing a two-dimensional tomographic image based on the stored RF signal frame data;
measuring displacement from plural sets of the stored RF signal frame data;
generating tomographic volume data by performing three-dimensional coordinate conversion based on a position of the constructed two-dimensional tomographic image;
collecting the plural sets of elastic volume data obtained by sliding on the scan plane of the ultrasonic wave to be transmitted to the object in the direction which intersects with the scan plane so as to generate elastic volume data;
generating elastic frame data by calculating elastic information indicating the hardness or softness based on the reflected echo signal measured by the ultrasonic probe and generating elastic volume data based on plural sets of elastic frame data;

displaying at least one of elastic slice images of a plurality of cross sections and an elastic rendering image generated based on the elastic volume data;

setting a plurality of three-dimensional regions of interest through at least one of the displayed elastic slice images of the plurality of cross sections and the displayed elastic rendering image; and calculating a three-dimensional elastic ratio between the elastic information in a set first three-dimensional region of interest and the elastic information in a set second three-dimensional region of interest, and displaying the calculated three-dimensional elastic ratio on the display;

calculating a two-dimensional elastic ratio between elastic information of a region corresponding to the first three-dimensional region of interest and elastic information of a region corresponding to the second three-dimensional region of interest in each of the plural sets of elastic frame data of the elastic rendering image; and calculating the three-dimensional elastic ratio based on the two-dimensional elastic ratio in each of the plural sets of the elastic frame data.

13. The three-dimensional elastic ratio calculating method according to claim 12, further comprising:

calculating the three-dimensional elastic ratio by averaging the two-dimensional elastic ratio calculated in each set of the elastic frame data.

* * * * *